(12) United States Patent
Parker et al.

(10) Patent No.: US 9,018,019 B2
(45) Date of Patent: Apr. 28, 2015

(54) ENGINEERED CONDUCTIVE POLYMER FILMS TO MEDIATE BIOCHEMICAL INTERACTIONS

(75) Inventors: Kevin Kit Parker, Waltham, MA (US); Megan O'Grady, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 745 days.

(21) Appl. No.: 12/443,894

(22) PCT Filed: Oct. 4, 2007

(86) PCT No.: PCT/US2007/021405
§ 371 (c)(1),
(2), (4) Date: Apr. 6, 2010

(87) PCT Pub. No.: WO2008/054611
PCT Pub. Date: May 8, 2008

(65) Prior Publication Data
US 2010/0191083 A1    Jul. 29, 2010

Related U.S. Application Data

(60) Provisional application No. 60/828,178, filed on Oct. 4, 2006.

(51) Int. Cl.
| | | |
|---|---|---|
| *G01N 33/544* | (2006.01) | |
| *G01N 33/545* | (2006.01) | |
| *A61B 5/0492* | (2006.01) | |
| *C09D 165/00* | (2006.01) | |
| *C09D 179/02* | (2006.01) | |
| *C12Q 1/00* | (2006.01) | |
| *G01N 33/543* | (2006.01) | |

(52) U.S. Cl.
CPC ............ *G01N 33/545* (2013.01); *A61B 5/0492* (2013.01); *C09D 165/00* (2013.01); *C09D 179/02* (2013.01); *C12Q 1/002* (2013.01); *G01N 33/5438* (2013.01)

(58) Field of Classification Search
CPC ............................. G01N 33/545; A61B 5/0492
USPC ........................................................ 436/535
See application file for complete search history.

(56) References Cited

U.S. PATENT DOCUMENTS

| | | | | |
|---|---|---|---|---|
| 4,476,004 A | * | 10/1984 | Pohl ........................... | 435/285.2 |
| 4,839,322 A | | 6/1989 | Yodice | |
| 5,403,451 A | * | 4/1995 | Riviello et al. ............. | 205/777.5 |
| 5,440,025 A | * | 8/1995 | Marx et al. .................... | 536/25.4 |
| 5,589,047 A | * | 12/1996 | Coster et al. ................. | 204/450 |
| 6,095,148 A | * | 8/2000 | Shastri et al. ................. | 128/898 |

(Continued)

*Primary Examiner* — Melanie Y Brown
(74) *Attorney, Agent, or Firm* — McCarter & English, LLP; Maria Laccotripe Zacharakis; Deborah L. Nagle

(57) ABSTRACT

The conductive polymer films of this disclosure reversibly and selectively mediate ligand-receptor interactions. This electrochemical manipulation of biochemical interactions is accomplished by embedding or adsorbing receptors for ligands of interest in or onto a conductive polymer matrix. The matrix can also be doped, for example, with desired ions, polyions, or surfactants. Depending on the receptor properties and dopants utilized, ligand-receptor interactions at the polymer-electrolyte interface are manipulated by controlling the oxidation and reduction of the conductive polymer. The intrinsic charge transfer characteristics of conductive polymers are used to modulate ligand-receptor interactions.

29 Claims, 23 Drawing Sheets

(56) References Cited

U.S. PATENT DOCUMENTS

| | | |
|---|---|---|
| 6,184,030 B1 * | 2/2001 | Katoot et al. ............... 435/287.2 |
| 6,344,333 B2 | 2/2002 | Gindilis et al. |
| 6,770,190 B1 * | 8/2004 | Milanovski et al. ....... 205/777.5 |
| 8,005,526 B2 * | 8/2011 | Martin et al. ................. 600/372 |
| 2001/0006749 A1 | 7/2001 | Shackle |
| 2003/0135166 A1 * | 7/2003 | Gonnelli ....................... 604/264 |
| 2003/0226996 A1 * | 12/2003 | Aramaki et al. ......... 252/62.3 Q |
| 2004/0092002 A1 * | 5/2004 | Kim et al. ................. 435/287.1 |
| 2004/0241752 A1 * | 12/2004 | Anderson et al. ............. 435/7.1 |
| 2005/0048651 A1 * | 3/2005 | Ryttsen et al. ................ 435/459 |
| 2006/0105399 A1 * | 5/2006 | Lawman et al. ............... 435/7.2 |
| 2007/0173901 A1 * | 7/2007 | Reeve ............................. 607/45 |
| 2009/0294290 A1 * | 12/2009 | Furusawa et al. ............. 204/547 |

\* cited by examiner

ENGINEERED CONDUCTIVE POLYMER FILMS TO MEDIATE BIOCHEMICAL INTERACTIONS

CROSS-REFERENCE TO RELATED APPLICATIONS

This application claims priority to U.S. Provisional Patent Application No. 60/828,178, filed Oct. 4, 2006, which is incorporated by reference into this disclosure in its entirety.

BACKGROUND

An emerging trend in biotechnology and medical diagnostics is to improve the speed and sensitivity of molecular analyses via label-free, noninvasive techniques that exploit electrochemical and microelectronic technologies. Label-free detection methods have been widely utilized to monitor analyte concentrations in vitro, most commonly using either ion-sensitive semiconductor field effect transistors or conductive polymeric devices. These label-free technologies are scalable, with the added advantage that they can be used to quantitatively measure a variety of molecular concentration gradients in a highly parallel fashion via surface modifications of individual electrodes. Furthermore, label-free detection technologies are advantageous over traditional optical and radiolabel techniques, since they can be used to monitor cells and tissues over long periods of time without the onset of cytotoxic side effects. Although the biocompatibility and high-throughput of label-free technologies are favorable, a critical downfall of existing devices is that they do not permit an investigator to actively mediate molecular binding at the sensor surface. Consequently, most label-free devices cannot be used to control adsorption of biomolecules to a functionalized surface in an on-off fashion, nor can these devices be used to dynamically detect molecular gradients within cell or tissue microenvironments.

SUMMARY

Towards this end, the conductive polymer films of this disclosure reversibly and selectively mediate ligand-receptor interactions. This electrochemical manipulation of biochemical interactions is accomplished by embedding or adsorbing receptors for ligands of interest in or onto a conductive polymer matrix. The matrix can also be doped or derivatized, for example, with desired ions, polyions, or surfactants.

Depending on the ligand-receptor interaction properties and dopants utilized, ligand-receptor interactions at the polymer-electrolyte interface are manipulated by controlling the oxidation and reduction of the conductive polymer. The intrinsic charge transfer characteristics of conductive polymers are used to modulate ligand-receptor interactions.

Further, the applications of the technology extend well beyond the biosensor applications currently exemplified. These films are coated onto surgical instruments to provide molecular sensitivity. These films and methods are useful to regulate analyte concentrations in solution and to regulate interactions on electrochemically complementary metal-oxide semiconductor (CMOS) microarrays and proteomics chips.

The films are flexible and biocompatible, thereby enabling their application in a variety of other applications. Further, the films, when disposed on instruments, are utilized for measurement and manipulation of components at scale levels ranging from nano- and micro-scales (e.g., from 10 nm to 10 microns) up to the cellular level or larger.

Improvements over previous devices include a significantly enhanced fabrication protocol, improved charge transfer kinetics, and conductive polymer films sensitive to a wide dynamic range of binding events (e.g., nanoscale range). Furthermore, the polymer films are highly sensitive and specific in their reversible binding. In studies using a fibronectin mAB ($\alpha$FN) doped polymer film, the film was selective for fibronectin only and non-specific adsorption was not significant. The extent of FN binding can be controlled by the voltage applied to the polymer; the polymer does not undergo morphological changes (impedance changes) when fibronectin is bound and subsequently released; the conductive polymer can be used to measure fibronectin concentrations in solution; and the minimum time period for FN-$\alpha$FN complexes to form is approximately 1-1000 milliseconds (ms), e.g., 30, 50, 100, 150, 200, 500, 750 ms, etc.

Devices containing a functionalized conductive polymer, e.g., a polymer that includes a target-specific binding moiety such as a receptor for a cell surface molecule or receptor for a subcellular target or an antibody specific for a target, are useful to move target compositions, e.g., cells characterized by a specific phenotype, from one location to another. The cell-specific receptor or cell-binding fragment thereof is coated onto or incorporated into the polymer. The receptor is an antibody or fragment thereof. For manipulation of cells, the antibody preferably binds to an epitope that is exposed on the surface of the target, e.g., the surface of a eukaryotic or prokaryotic cell such as a pathogenic bacterium or fungus or the surface of a particle such as a coat protein of a viral particle. The antibody is a polyclonal antisera or preferably a monoclonal antibody. Not only an intact monoclonal antibody, but also an immunologically-active antibody fragment, e.g., a Fab or (Fab)$_2$ fragment or an engineered single chain FV molecule is used to functionalize the conductive polymer. The conformation of the antibody molecule or receptor is electronically controlled to direct binding or release of its cognate antigen or ligand in a reversible manner. The rate of binding is controlled by the voltage applied to the polymer; i.e., the operator controls manipulations with a voltage "throttle" or potentiostat, thereby manipulating the oxidation and reduction state of the receptor-doped polymer.

Accordingly, a method for selectively moving a target cell includes the steps of contacting a heterogenous population of cells with a device containing a functionalized conductive polymer, applying an electrical current (e.g., a positive or negative charge) to the polymer thereby binding the cell to the device, and displacing the device from a first location to a second location. This process leads to displacement of the target cell from heterogenous population. Thus, moving the device and changing the charge applied to the polymer releases the cell at a second location.

This process is useful in a variety of medical applications such as physically separating tissues during surgery, e.g., pulling away target tissue from nerves so as not to damage such tissues during spinal cord surgery. When the device is a microsurgical device such as a scalpel, the scalpel surface is derivatized with a conductive polymer containing a receptor or other binding compositions such as an antibody that binds to a tumor-specific antigen. The tumor is excised, and upon application of an electrical charge, any residual tumor cells that become dislodged from the tumor mass bind to the scalpel and are removed from the body thereby reducing the risk of metastasis from residual tumor cells. Not only does the device act as a sensor to identify target cells, it also functions as an actuator to physically manipulate, e.g., move, identified target cells on an individual cell basis. The mechanical flexibility of functionalized devices, e.g., a scalpel, needle, trocar, catheter, and other devices for manipulating bodily tissues allow precision manipulations in minimally invasive procedures and permits real-time biopsies at tumor sites, e.g., breast lumps, subcutaneous tumors, in which the borders of diseased tissue is sensed and communicated to the operator as the device contacts individual cells. This real time diagnostic and therapeutic application is faster and more accurate than standard excision followed by standard analysis conducted in a pathology laboratory. For example, a functionalized biopsy needle is placed into or onto the tissue to be interrogated, and a signal, e.g., an audible sound such as 'click' or 'beep' or a visible indicator such as a flash or pulse of light, indicates a binding event with a tumor-specific receptor. As the tumor cells are sensed, the device is used to remove the tumor cells from the site. In another example, a derivatized device is useful to purge tumor cells from a patient-derived population of bone marrow cells prior to infusion into the patient in order to reconstitute immune cells after radiation therapy. In one embodiment, the device is optionally coupled with a laser; in another embodiment the device does not comprise a laser.

Some devices are configured for implantation into the body. For example, a defibrillator or pacemaker device is coated with the functionalized conductive polymer and placed into the body of a subject suffering from or at risk of developing irregular heart rhythm or abnormal heart function. Compositions embedded or on the polymer promote to improve vasomotor tone.

In addition to cell-by-cell manipulations, the devices are useful to manipulate components on a subcellular basis. A method for selectively moving a subcellular component of a cell, e.g., an organelle such as a mitochondria or nucleus, is carried out by contacting the subcellular component in an intracellular environment with a device containing a functionalized conductive polymer and applying an electrical current to the polymer. A subcellular structure is moved using a device with a polymer containing a ligand specific for the target structure. The devices are optionally coupled to a microscope, e.g., an atomic force microscope.

On a molecular level, components of a solution are manipulated with molecular specificity. The polymers permit construction of a molecular factory. For example, mRNA transcripts are embedded into or coated onto the polymer and translation of the message into protein is electrically controlled. This technique is used to rapidly and efficiently produce recombinant proteins for therapeutic and other uses.

An advantage of the devices described herein is that unlike other microelectrical mechanical systems, these devices function with precision and specificity in an aqueous environment thereby permitting numerous biological and medical applications. The devices and polymeric structures are scalable from a nanoscale (e.g., 1, 10, 20, 50, 100 nm) to a centimeter scale. Additional advantages include flexibility and biocompatibility.

Other features and advantages of the invention will be apparent from the following description of the preferred embodiments thereof and from the claims. All references cited herein are hereby incorporated by reference.

BRIEF DESCRIPTION OF THE DRAWINGS

The foregoing and other features and advantages of the invention will be apparent from the following, more-particular description. In the accompanying drawings, like reference characters refer to the same or similar parts throughout the different views. The drawings are not necessarily to scale, emphasis instead being placed upon illustrating particular principles, discussed below.

DETAILED DESCRIPTION

Components and Materials

Figure 1:
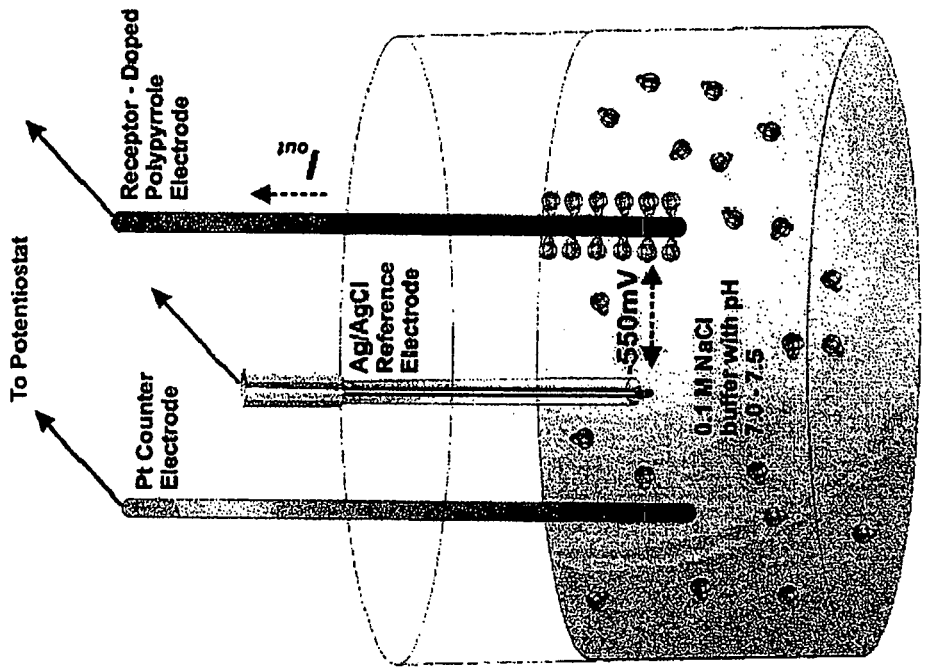
FIGS. 1 and 2 illustrate control of ligand-receptor interactions in a conductive polymer film.

Receptors for ligands of interest are embedded in coated or adsorbed to a conductive polymer film that can be formed via electropolymerization. First, a monomer from which a conductive polymer is formed and receptors are added to a physiological salt buffer solution along with dopant ions, polyions or surfactant molecules. Three electrodes (a working electrode, a reference electrode, and a counter electrode) are inserted into the solution. When a voltage is applied to the electrodes, the monomer polymerizes as a conductive film on the surface of the working electrode with the receptors and dopants entrapped therein or adsorbed thereto.

The ligand of interest, with which the receptor will interact, can be, for example, a protein, enzyme, analyte, biomolecule, DNA, mRNA, fatty acid, drug compound or synthetic peptide. In one particular example, the ligand of interest is fibronectin (FN) protein.

The receptor is complimentary to the ligand of interest and can be a monoclonal or polyclonal antibody, ssDNA or mRNA sequence, enzyme inhibitor, affinity probe, drug target, protein or biomolecule binding domain. In one particular example, the receptor is a monoclonal anti-fibronectin antibody. Examples of receptors suitable for other applications, such as peptides for tumor antigens, are listed, infra. The minimal size of the receptor molecules that can be embedded in conductive polymers is as low as 5, 10, 15 or 20 nucleotides. For example, Ramanavicience et al. ("Pulsed amperometric detection of DNA with an ssDNA/polypyrrole-modified electrode." *Analytical and Bioanalytical Chemistry* 379: 287-293, 2004) demonstrated that 20-mer single-stranded DNA oligonucleotides can be entrapped in polypyrrole conductive polymer matrices and retain their biological specificity. Short peptides, 2, 5, 10, 20, 50 or more residues in length are associated with the conductive polymer. Proteins of any size, e.g., a heterodimeric antibody (150,000 daltons), are particularly useful for identifying and manipulating target cells. Antibody fragments, e.g., antibody binding fragments or single chain antibodies are also useful for identifying and manipulating target cells. Prior to this invention, approximately 6 kDa represented the smallest biomolecules entrapped in polymer matrices to date. Various enzymes have also been electropolymerized in conductive polymer films, but the size of these enzymes is upwards of approximately 60 kDa. Others have entrapped ions, polyions, and surfactants in conductive polymer films that are smaller than 6 kDa, but retention of their molecular specificity and correct conformations during electropolymerization has been uncertain. Improvements over these and other earlier methods include a significantly enhanced fabrication protocol, improved charge transfer kinetics, and conductive polymer films sensitive to a wide dynamic range of binding events (e.g., nanoscale range).

The physiological salt buffer solution is pH neutral (i.e., the pH is in the range of about to 7 to about 7.6). The solution includes a sodium chloride (NaCl) concentration that is significantly higher than other compounds in the buffer. In one example, the buffer solution is Tyrode's solution, which has the following ingredient concentrations (in mmol/L): 135 NaCl, 5.4 KCl, 1.8 $CaCl_2$, 1 $MgCl_2$, 0.33 $NaH_2PO_4$, 5 HEPES (4-(2-hydroxyethyl)-1-piperazineethanesulfonic acid), and 5 glucose.

Dopant ions, polyions, and surfactant molecules are added to the buffer solution to facilitate either cation or anion exchange, depending on the ligand-receptor interaction of interest. For example, for ligand-receptor interactions where both the ligand and the receptor are positively charged, anionic dopants are incorporated into the conductive polymer matrix. Conversely, for ligand-receptor interactions where both the ligand and the receptor are negatively charged, cationic dopants are utilized. Examples include anionic dopants such as $Cl^-$, $NO_3^-$, $ClO_4^-$, $SO_4^-$, or dodecylbenzene sulfonate and cationic dopants such as $Na^+$, $N^+$, cetyltrimethylammonium chloride, dodecyltrimethylammonium chloride, or octyltrimethylammonium chloride. Positively charged dopants are incorporated into or onto the polymer (including positively charged proteins, antibodies, ligands, etc.), such that positively charged protein-protein interactions are facilitated. Using this method, positively charged dopants are reliably deposited onto or incorporated into the polymer despite the observation that positively charged interactions can be harder to control due to polymer formation via an oxidation procedure in which the addition of electrons is key. Therefore, negatively charged dopants with excess electrons are most easily incorporated into the polymer. An exemplary method for getting around this is by using a surfactant as a dopant with hydrophobic moieties and a positively charged functional group.

The conductive polymer film, in which the receptors and dopants are embedded, includes a polyene backbone. Examples of the conductive polymer include polyacetylene, polyaniline, polypyrrole, polythiopene, and poly(p-phenylene). Polypyrrole is a preferred conductive polymer for making electrochemical actuators for the following reasons: (1) polypyrrole is biocompatible and, hence, causes minimal and reversible disturbance to the working environment; (2) polypyrrole is capable of transducing the energy arising from interaction between immune reagents into electrical signals that are easily monitored; (3) polypyrrole protects electrodes from fouling and interfering materials such as electroactive anions; and (4) polypyrrole can be modified in situ in a controlled fashion. Polyaniline and polythiophene are also commonly used to fabricate electrochemical biosensors. Polythiophene is grown from organic solvents in which the monomer is soluble, and polyaniline is polymerized in acidic conditions. Both polymers are biocompatible following electrochemical or chemical polymerization.

The following is a non-exhaustive list of conductive, biocompatible polymers in which:

1) receptors for ligands of interest are entrapped in the conductive polymer matrix, or 2) receptors for ligands of interest are adsorbed at the surface of the conductive polymer:
    polyaniline;
    polypyrrole;
    polythiopene;
    polydiaminobenzene;
    polyacetylene;
    poly-(p-phylene);
    poly(terthiophene-carboxilic acid);
    poly (ortho-phenylenediamine);
    poly (dichlorophenolindophenol);
    poly(indole);
    poly(3,4-ethylenedioxythiophene) (PEDOT);
    poly(pyrrole-benzophenone);
    poly (amphiphilic pyrrole) films;
    poly (pyrrole-flavin) films;
    poly(pyrrole-biotin) films;
    poly-2-aminoaniline;
    polybithiophene;
    polyazulenes;
    poly(N-vinyl amide) copolymer films made of N-vinylpyrrolidine (NVP) and Nvinylphthalimide (NVPH);
    poly (thionine);
    poly (tryptophan);
    poly(tyramine);
    poly(Nile Blue);
    methylene green (PMG) redox film;
    poly(3-methylthiophene);
    Conductive, biocompatible polymer films functionalized with the following redox mediators: ferrocene, ruthenium, osmium, transferring and viologen;
    Polypyrrole functionalized by an N-hydroxy-phthalimide activated esters, such as poly(tris bipyridine ruthenium complex) film and poly (m-phenylenediamine)/polypyrrole composite films;
    Conductive, biocompatible polymer films functionalized with esters able to form an amide bond with biomolecules containing amino groups; examples of esters able to form an amide bond with biomolecules containing amino groups include N-hydroxysuccinimide and N-hydroxyphthalimide;
    Conductive polymer films bearing tethered activated esters or amine or carboxy groups;
    Poly(dicarbazole) films, such as chiral electropolymerizable dicarbazole derivatives functionalized by N-hydroxysuccinimide, N-hydroxyphthalimide or pentafluorophenoxy groups;

Conductive, biocompatible copolymer films, such as polyphenols, poly (o-phenylenediamine), polyphenols, or polyphenylenediamines and conductive polymer hybrids; and Azine derivatives electropolymerized from aqueous solutions, such as phenazines, phenotiazines and phenoxazines, Methylene Blue, thionine and Meldola Blue.

Several of the polymers listed are derivatives of polypyrrole or polyaniline. Methods for manipulating the polymer structure to enhance the sensitivity of various conductive polymer biosensors are known in the art. These polymers are synthesized in monomer or polymer form. Other polymers can also be used.

The working electrode, on which the polymer film is formed, has a metallic surface, formed, e.g., of gold or platinum of high purity (99.99% or greater purity). The reference electrode, which is used to measure the working electrode potential, is formed of Ag, AgCl or saturated calomel ($Hg_2Cl_2$). Finally, the counter electrode, which serves to complete the electrical circuit, can be a large wire or plate; the counter electrode serves to enhance the delivery/removal of electrons to/from the polymer surface.

A potentiostat, which serves as a voltage source, is coupled with the electrodes. The potentiostat is capable of performing each of the following: impedance spectroscopy up to 200 kHz, pulse voltammetry, DC potential amperometry, chronovoltammetry, normal pulse voltammetry, and open circuit potential measurements.

Fabrication and Characterization of Conductive Polymer Electrodes

The electrodes are cleaned prior to use by washing them with ultra-pure (18 MΩ) water followed by sonication for two minutes. The electrodes are then attached to the potentiostat in a three-electrode cell configuration. The monomer (e.g., polypyrrole monomer) is electropolymerized galvanostatically (at constant current) to form the conductive-polymer film on a metal electrode.

The receptors and any dopant molecules become entrapped in the conductive-polymer matrix during polymerization. After electropolyermization, the gold/conductive polymer/ receptor electrode is rinsed with ultrapure (18 MΩ) water. Electrodes are deprotonated in a pH-calibrated physiological buffer solution with 1% bovine serum albumin (BSA) for more than 20 hours prior to an experiment, in order to inhibit non-specific binding and to condition the electrodes.

When characterizing the impedance response of the receptor-doped conductive polymers, stepped potentiostatic impedance spectroscopy scans (SPEIS) are conducted. During ligand binding/dissociation experiments, the receptor-doped conductive polymer is held at a reduction state in order to inhibit receptor-ligand interactions. The functionalized polymer is then held at an oxidizing potential for 10 seconds, which is a reasonable time period to observe slow mass transfer interactions, such as ligand adsorption to the polymer. After 10 seconds, the polymer film is reduced for 90 seconds once again, wherein dissociation of ligands from the polymer occurs. Control experiments are also performed with only the physiological buffer and no ligands present, in order to observe any changes in polymer oxidation/reduction when no ligands are present in solution.

The ability of a receptor-doped conductive polymer to bind and release cells depending on its oxidation and reduction state is tested by seeding cells in the presence of a functionalized electrode. Pluronics F-127 is utilized to block binding to a tissue culture dish, such that cells can only bind to the polypyrrole electrode. Cells are fluorescently tagged and imaged over the course of two to six hours immediately after plating. Toggling of the electrode oxidation and reduction will allow binding/release of the cell.

Applications

The conductive polymer film is fabricated into a functionalized instrument for use in surgery and other contexts. In one example, a "smart" surgical instrument in the form of, e.g., a scalpel, needle or a metallized probe is functionalized with a receptor-doped polypyrrole film that binds and removes analytes, cells, and tissues with molecular specificity. Any diseased cell with an identifiable molecular marker can be removed with such an instrument. In one example, such an instrument selectively removes cancer cells from a tumor, while leaving healthy cells intact, when a positive electric potential is applied. The functionalized instrument also detects and removes non-excised tumor cells (e.g., micrometastases) and tissue following invasive surgery, wherein the instrument extricates remaining metastases without destructively interfering with normal cell or tissue function. Accordingly, the instrument acts not merely as a sensor, but also as an active transport mechanism for the cells or other components of interest. In other applications, the instrument performs real-time biopsies of breast lumps, subcutaneous tumors, etc. Accordingly, samples need not be sent to a pathology lab to be read; instead a functionalized biopsy needle can be configured to provide a sound (e.g., a "beep" or a "click") when binding to tumor antibody (due to, e.g., a change in voltage); and the tumor is removed right then.

Although many tumor-specific antigens have been identified from melanomas, only a few tumor-specific antigens have been isolated from breast, prostate and epithelial cancers due to the difficulty in generating specific, tumor-reactive T cells. However, tumor-specific antigens identified in melanomas have been shown to be frequently expressed in breast, prostate, bladder, lung and testicular cancers. Below, in Table 1, is a list of human tumor antigens common to many human cancer types (tumor-specific shared antigens); Table 2 provides a list of tumor-specific antigens specific to human melanomas only. The peptide sequences, listed below, are embedded in the polymer films and are the established peptide sequences of the tumor-specific antigens that have been targeted by various immunotherapies.

TABLE 1

Tumor-Specific Shared Antigens.

| Antigen | Peptide Sequence |
|---|---|
| MAGE-1 | EADPTGHSY |
|  | SAYGEPRKL |
| MAGE:-3 | EVDPIGHIY |
|  | FLWGPRALV |
|  | MEVDPIGHAY |
| GAGE | YRPRPRRY |
| BAGE | AARAVFLAL |
| RAGC | SPSSNRIRNT |
| NYESO-1/GAG3 | (Q)SLLMWITQG{L} |
| ORF1 | ASGPGGGAPR |
| ORF2 | LAAQERRVPR |
|  | MLMAQEAIAH |

TABLE 2

Melanoma-Specific Antigens.

| Antigen | Peptide Sequence |
|---|---|
| Tyrosinase | MLLAVLYCL |
|  | YMNGTMSQV |
|  | SEIWRDIDE |
|  | AFIPWHRLF |
|  | KCDICFDEY |
|  | SSDYVIPIGTY |
| MART-1/Melan-A | AAGIGIITV |
|  | FAAGIGILTV |
|  | AEEAAGIGILTV |
| gp100 | KTWGQYWQV |
|  | ITDQVPFSV |
|  | YLEPGPVTA |
|  | LLDGTATLRL |
|  | VLYRYGSFSV |
|  | RLMKQDFSV |
|  | RLPRIFCSC |
| gp75/TRP4 | MSLQRQFLR |
| TRP-2 | LLPGGRPYR |
|  | LLPGGRPYR |
|  | SVYDFFVWL |

Table 3, below, identifies additional markers for different types of tumors.

TABLE 3

| Tumor Type | Marker | Citation |
|---|---|---|
| Ovarian | tetranectin<br>YKL-40<br>Cancer Associated<br>Serum Antigen<br>CA-125 | Gronlund, B., et al., Pre-treatment prediction of chemoresistance in second-line chemotherapy of ovarian carcinoma: value of serological tumor marker determination (tetranectin, YKL-40, CASA, CA-125) INT J Biol Markers. 21(3): 141-8 (2006) |
| TBD | Secretagogin (hexa EF-hand protein) | Rogstam, A. et al., Binding of calcium ions and SNAP-25 to the hexa EF-hand protein secretagogin. Biochem J. Aug, 2006 |
| Laryngeal Squamous Cell Carcinoma | p53<br>bcl-2<br>CD34<br>CD44H<br>CD44v6<br>Ki-67 | Spafford, M. F. et al., Correlation of tumor markers p53, bcl-2, CD34, CD44H, CD44H, and Ki-67 with survival and metastasis in laryngeal squamous cell carcinoma. Arch Otolaryngol Head Neck Surg. 122(6) (1996). |
| Hodgkin's Lymphoma | CD30 | Smith, CA. et al., CD30 antigen, a marker for Hodgkin's Lymphoma, is a receptor whose ligand defines an emerging family of cytokines with homology to TNF. Cell. 73(7): 1349-60 (1993). |
| Prostate Cancer | Prostate Stem Cell Antigen (PSCA) | Reiter, Robert E. et al., Prostate stem cell antigen: A cell surface marker overexpressed in prostate cancer. PNAS 95, 1735-1740 (1998) |
| Prostate Cancer | ALCAM/MEMD/CD166 | Ruan, Weiming, et al., Identification of clinically significant tumor antigens by selection phage antibody library on tumor cells in situ using laser capture microdissection. MCPO (2006) |
| Gastric Cancer | AFP<br>CEA<br>CA-199 | Choi, Seok Reyol, et al., Role of serum tumor markers in monitoring for recurrence of gastric cancer following radical gastrectomy. Dig Dis Sci (2005 or 2006) |
| Colorectal Carcinoma | CD34<br>CD105<br>NOS<br>HIF-1α | Yu, Jian-Xian, et al., Expression of NOS and HIF-1α in human colorectal carcinoma and implication in tumor angiogenesis. World J. Gastroenterol. 12(29): 4660-4664 (2006) |

In other applications, a functionalized instrument coated with the receptor-doped polymeric film is used to bind and remove any of the following from the body: infectious bacteria and plaques, e.g., arteriosclerotic plaques, toxins, fatty deposits, and various analytes and hormones. For example, the instrument contains a ligand, e.g., an antibody or fragment thereof, that binds to a cell-surface or particle-surface antigen of a bacteria or virus, respectively. To disrupt and/or remove arteriosclerotic plaques, a vascular catheter or stent is coated (functionalized) with a ligand that binds to or associates with lipoproteins or other plaque compositions. Non-limiting examples of other devices for the removal of blood vessel plaque which may be functionalized are microactuators and balloon stents. Non-limiting examples of plaque components to which an attached ligand can bind include lipids, calcium, platelet cell factors, white blood cell factors, cholesterol, and cholesterol binding proteins.

Such a tool can further be used to control and regulate the levels of various analytes and hormones in vitro and in vivo. For example, the tool can be used to measure and regulate the amount of glucose in blood by selectively binding and releasing the glucose into the blood. In another application, a functionalized instrument of this description can likewise be used to control the levels of enzymes, proteins, hormones, or biomolecules present in a bioreactor. In each of these applications, the instrument is provided with a "throttle" control, wherein the concentration of the ligand in solution is incrementally increased by incrementally reducing the electric potential applied to the instrument, and wherein the concentration of ligand can be incrementally decreased by incrementally increasing the electric potential applied to the instrument.

In still another application, the functionalized instrument is used to traffic and deliver organelles, biomolecules, hormones, and/or proteins to cells and tissues by increasing and decreasing the potential applied to the conductive polymer film. For example, the instrument can remove organelles, biomolecules, hormones, and/or proteins from existing cells or tissues and to selectively transplant and release them into 'acceptor' cells or tissues.

In other embodiments, a polymer film doped with receptors is used in microarrays and proteomics chips. For use in these applications, polypyrrole is doped with a single-stranded DNA sequence (ssDNA) of interest; and mRNA concentrations can be quantified based on their ability to bind to the ssDNA sequence entrapped in the polypyrrole matrix. In this context, the concentration of mRNA is quantified electrochemically instead of employing exogenous fluorescent labels. Specifically, mRNA binding alters the amount of current transmitted from the polypyrrole to the sensing electrode (i.e., as more mRNA is bound, the current decreases). Consequently, the binding of mRNA is detected by measuring the current flow through the electrodes.

The doped polymer film is combined with microelectrode and CMOS technologies to build an electrochemical, reversible microarray with different gene sequences on each electrode in the array. Changes in current at various electrodes accordingly correspond to differing mRNA concentrations bound to ssDNA at each electrode. Because the binding process is reversible (by changing the voltage on the electrodes), dynamic changes in mRNA concentrations are detected. Use of a receptor-doped polymer film in a microarray provides a cheaper, faster and re-useable alternative to fluorescently labeled microarrays.

Similarly, polypyrrole is doped with a receptor or amino acid sequence for biomolecules of interest on a microelectrode/CMOS chip for proteomics technologies. Different receptor or amino acid sequences are provided on each microelectrode in the array; changes in current at various microelectrodes correspond to differing protein concentrations. The binding is reversible, such that dynamic changes in protein concentrations can be detected. This chip offers a cheaper, faster and re-useable alternative to fluorescently-labeled proteomics chips.

CMOS proteomics chips incorporating the doped polymer are used to dynamically monitor analyte concentrations in vivo. Different receptor or amino acid sequences are again provided on each electrode in the array. Changes in current at various electrodes correspond to differing protein concentrations at each electrode. Binding of the protein is reversible, such that dynamic changes in protein concentrations can be detected. The process again is re-useable and cheaper and faster than existing techniques. The apparatus is packaged to serve as an implantable device.

In yet another application, the receptor-doped polymer can be implanted in an organism (e.g., a human) and used to measure and selectively control levels of drugs (or glucose or analytes) in the body. If the polypyrrole is functionalized to interact with the drug of interest, the release and circulating levels of a drug can be controlled by altering the voltage applied to the polypyrrole.

Although conductive polymers have been widely used to sense and detect analyte concentrations, the ability to of conductive polymers to reversibly and controllably mediate biochemical interactions remains to be exploited in commercial technologies. The ability to electrochemically manipulate biochemical interactions is applicable to the development of macroscale and microscale surgical instruments with molecular sensitivity, as well as electrochemical complementary metal-oxide semiconductor (CMOS) microarrays and proteomics chips. Various applications of engineered conductive polymer films specifically employed to modulate ligand-receptor interactions are listed below.

Figures 16, 17, 18:
FIGS. 16-20 illustrate the operation of a polypyrrole "smart" scalpel.
Figures 19, 20:
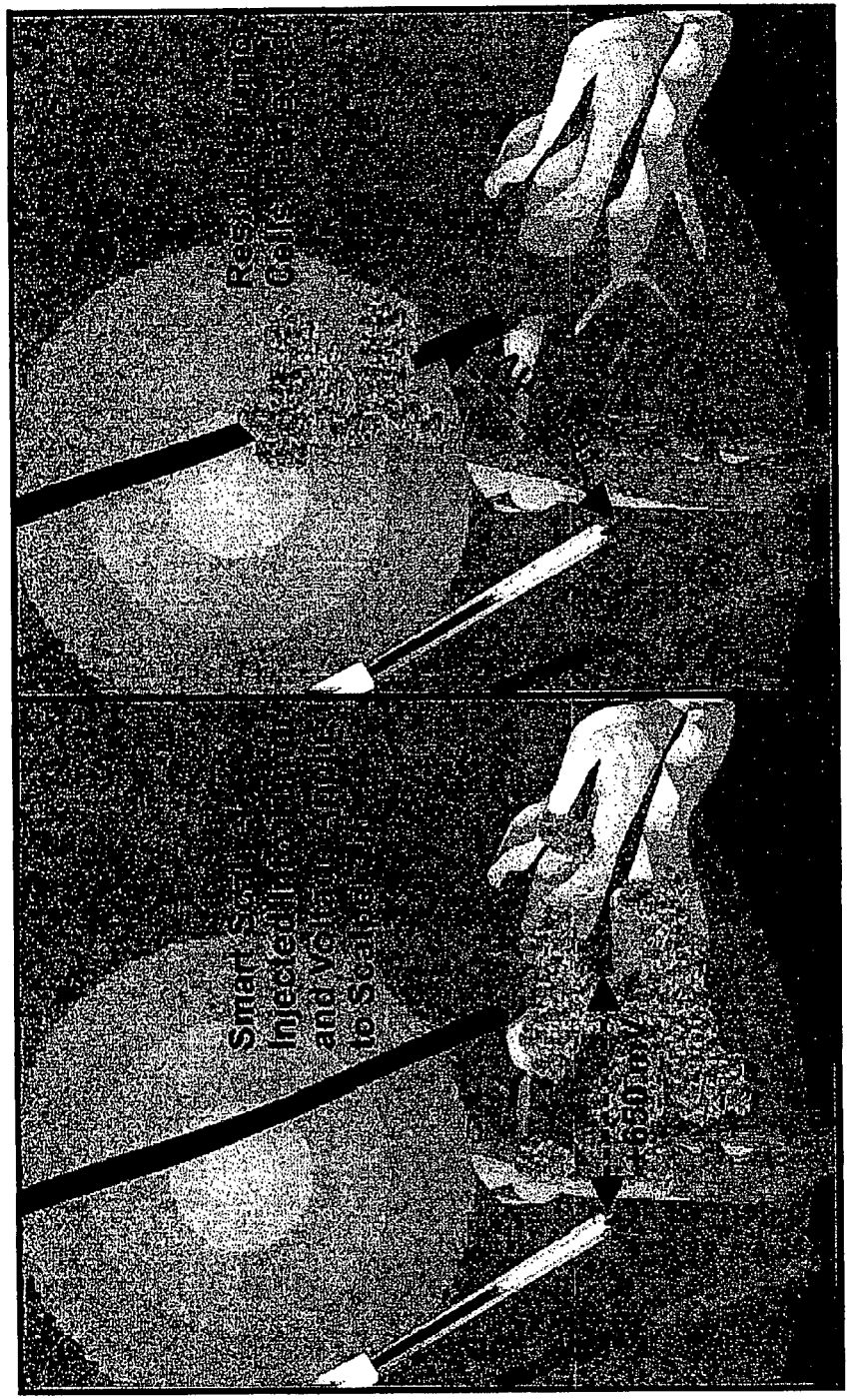
Figure 21:
FIGS. 21-25 illustrate the fabrication of conductive cantilevers functionalized with a conductive polymer.

Surgical removal of a tumor is illustrated in FIGS. 16 and 17, followed by operation of a polypyrrole "smart scalpel" to remove residual tumor tissue in FIGS. 18-20. The metal scalpel is functionalized with a conductive polymer and specific receptors for a cell type, bacteria or toxin of interest. The scalpel is placed close to the desired tumor or bacterial infection, and a voltage is applied to the conductive polymer surface such that cells, bacteria or toxins selectively bind to the polypyrrole (FIGS. 18 and 19). The tumor, bacteria, or toxin can then be removed from its native environment without destructively interfering with normal cell or tissue function (FIG. 20). This technology can be used to bind and selectively remove non-excised tumor tissue, infectious bacteria or plaques, toxins with well-characterized chemical structures, and fatty deposits. These "smart" functionalized metallic probes are used to control and regulate the in vitro and in vivo levels of various hormones and paracrine signaling molecules.

Figures 32, 33:
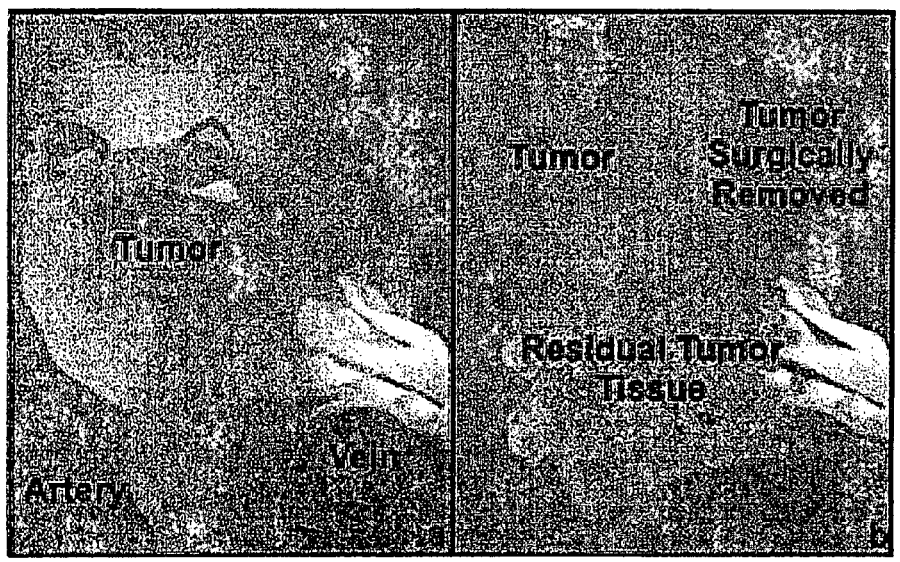
FIGS. 32-35 illustrate another operation wherein a smart scalpel is used to remove non-excised tumor tissue.
Figures 34, 35:
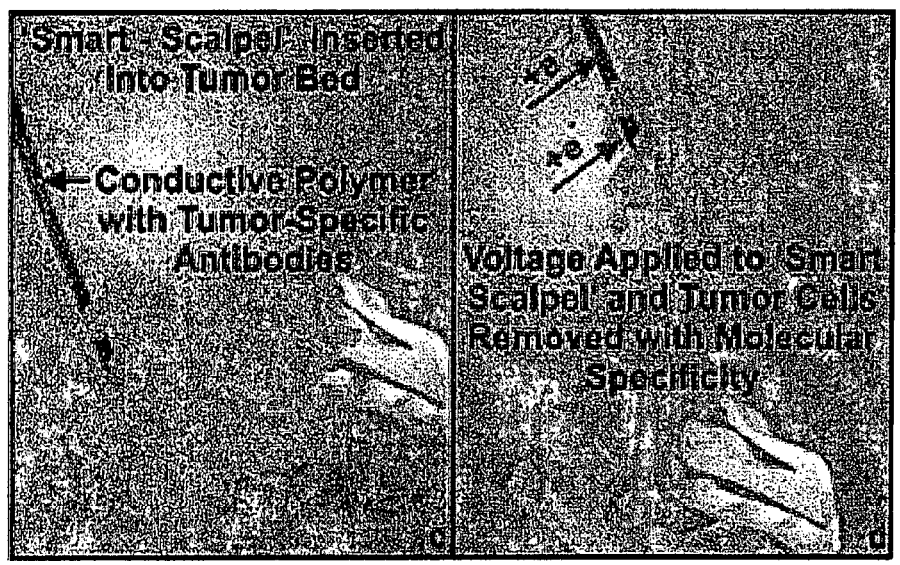

Another operation wherein a "smart scalpel" is used to remove non-excised tumor tissue is illustrated in FIGS. 32-35. The schematic illustrations show a tumor before (FIG. 32) and after surgical removal (FIG. 33). After surgical removal of a tumor, residual tumor tissue remains at the tumor site (FIG. 33). Left untreated, this residual tumor tissue can prove to be extremely malignant, growing and metastasizing in the body. A conductive polymer scalpel or biopsy probe doped with antibodies or peptide sequences specific for tumor cells markers is placed in the tumor bed (FIG. 34). A voltage is applied to the conductive polymer (FIG. 35) such that the tumor cells selectively bind to the conductive polymer. The tumor, bacteria, or toxin is then removed from its native environment without destructively interfering with normal cell or tissue function.

Figure 22:
Figure 23:
Figure 24:
Figure 25:
Figure 26:
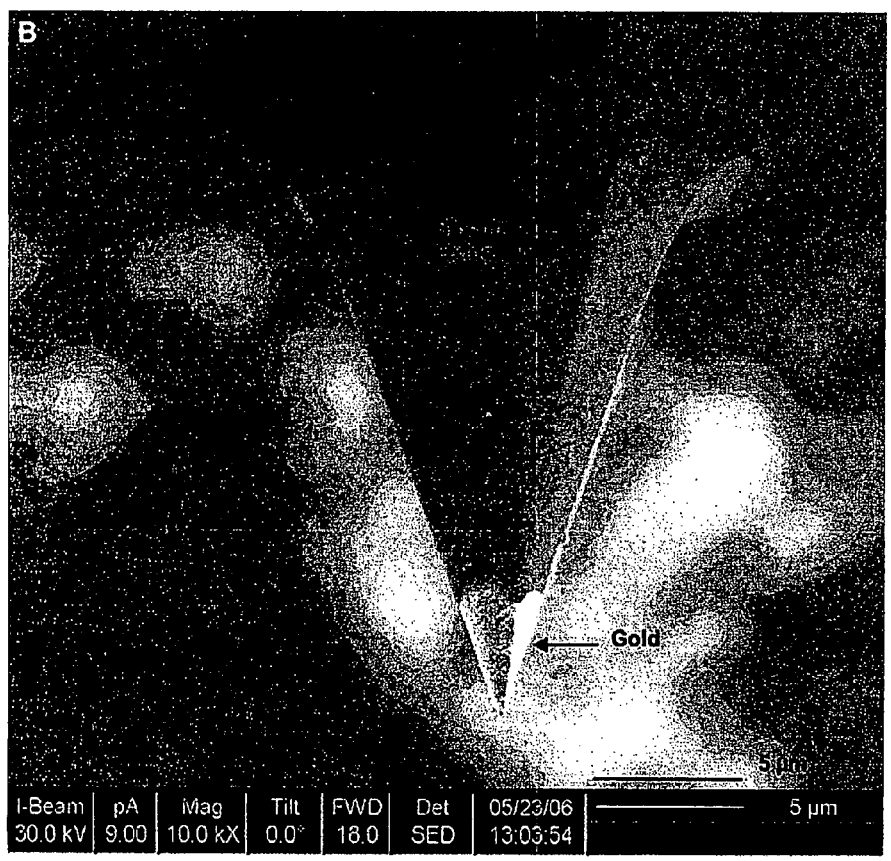
FIG. 26 is an image of a conductive AFM cantilever, following the fabrication procedure outlined in FIGS. 21-24.

The stages of fabrication of a conductive cantilever functionalized with a conductive polymer are illustrated in FIGS. 21-25. The starting substrate, shown in FIG. 21, can be a silicon or silicon nitride cantilever. A conducting metal layer (e.g., of platinum or gold) is then deposited, as shown in FIG. 22. An insulating layer of polysilicon, silicon, silicon oxide, silicon nitride, or parylene is subsequently deposited, as shown in FIG. 23. Etching with a focused ion beam exposes the underlying metal layer at the cantilever tip, as shown in FIG. 24, such that a conductive polymer can be electropolymerized only at the exposed metal regions, as shown in FIG. 25. An image of a conductive atomic-force-microscope (AFM) cantilever, following the fabrication procedure outlined in FIGS. 21-24 but without the conductive polymer layer at the AFM tip, is provided in FIG. 26.

Figure 27:
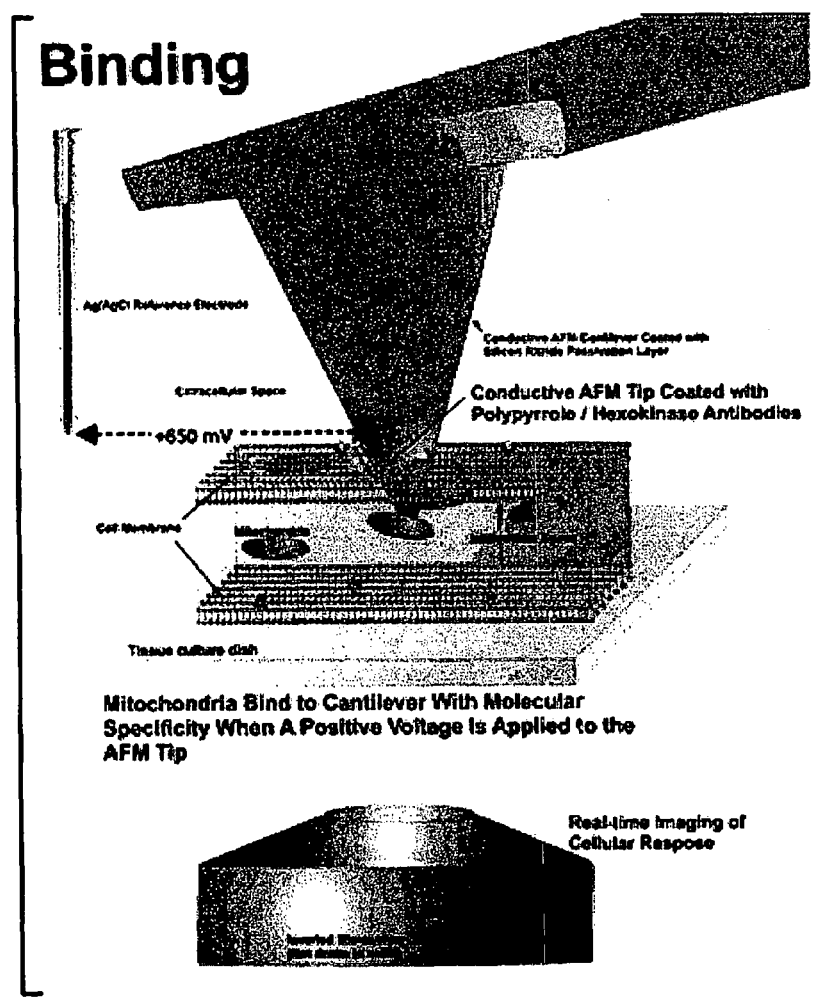
FIGS. 27-29 illustrate the use of a conductive polymer-coated sensor/actuator to traffic and deliver organelles between cells or tissues with molecular precision.
Figure 28:
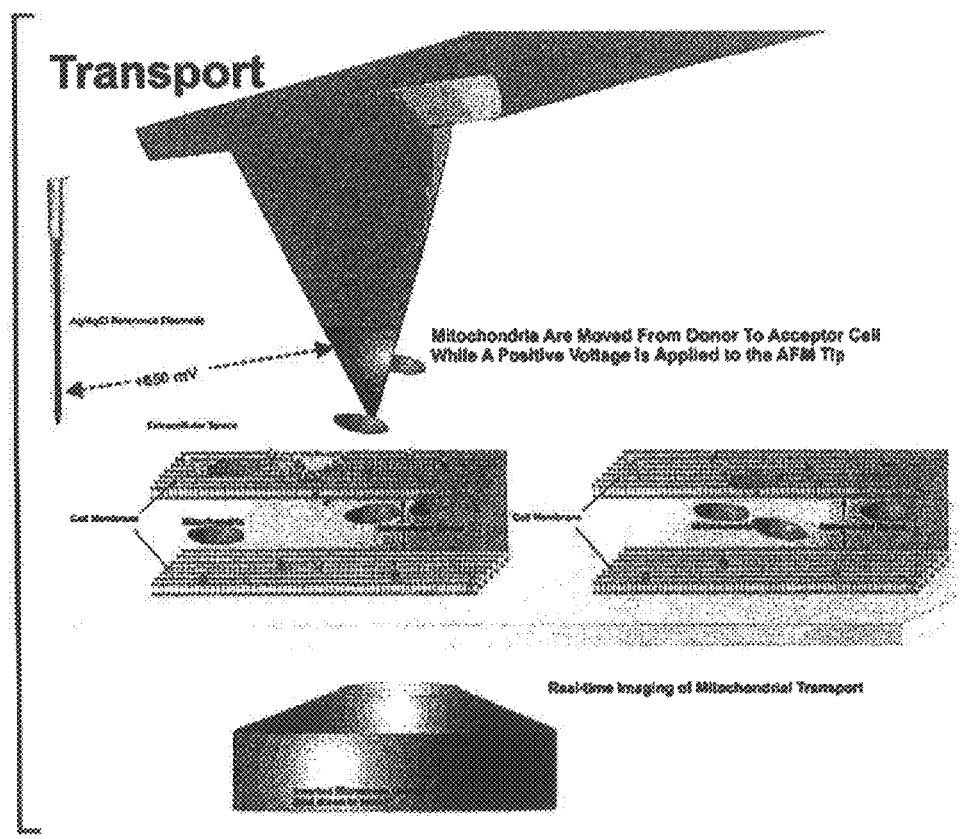
Figure 29:
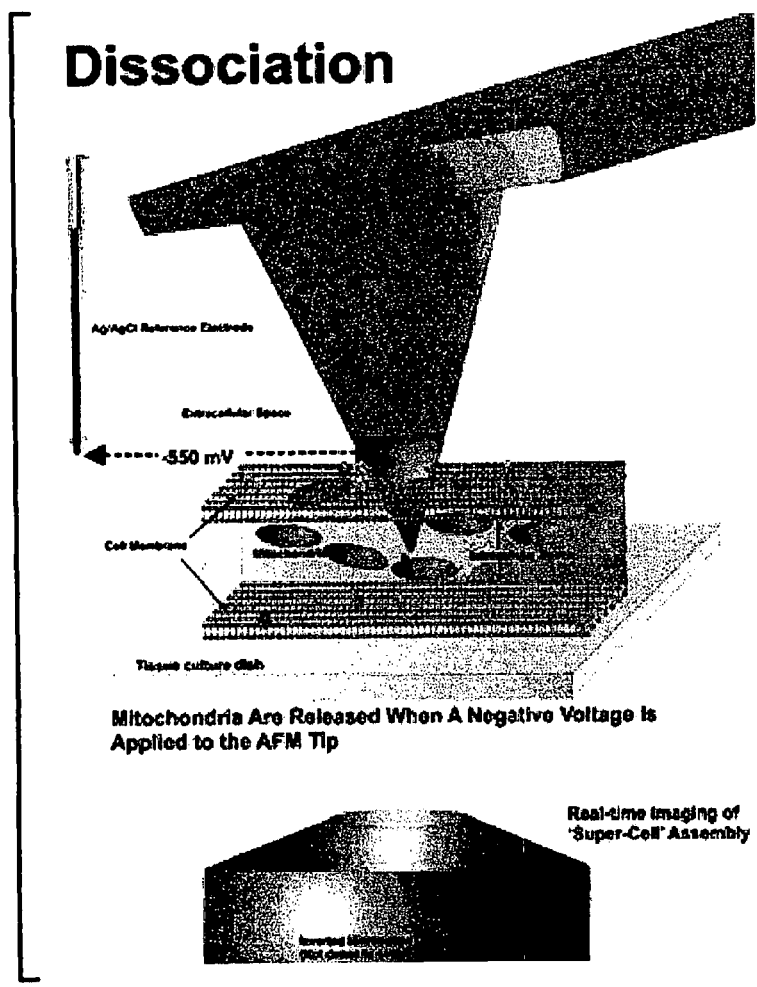

Use of a conductive polymer-coated sensor/actuator to traffic and deliver organelles between cells or tissues with molecular precision is illustrated in FIGS. 27-29. A metallized sensor or conductive AFM cantilever (produced, e.g., via the above-described method) is coated with a receptor-doped conductive polymer and placed in a cell. Once inside the cell, a positive voltage is applied to the conductive-polymer-coated electrode such that ligands (e.g., biomolecules, hormones, organelles, proteins, or DNA) will bind to the receptors embedded in the polypyrrole. Once bound, the metallized probe or conductive AFM cantilever is moved to an acceptor cell or tissue, while a positive potential is applied in order to keep the ligands of interest bound to the conductive polymer. The metallized probe or conductive AFM cantilever is then placed into an "acceptor" cell or tissue. Once a negative potential is applied to reduce the conductive polymer, the ligands of interest are released into the acceptor cell or tissue, thus completing the process of trafficking and delivering ligands or organelles between cells or tissues. This procedure is employed to transfer mitochondria between cells (as shown in FIGS. 27-29) in order to assemble a metabolic super-cell.

Figure 30:
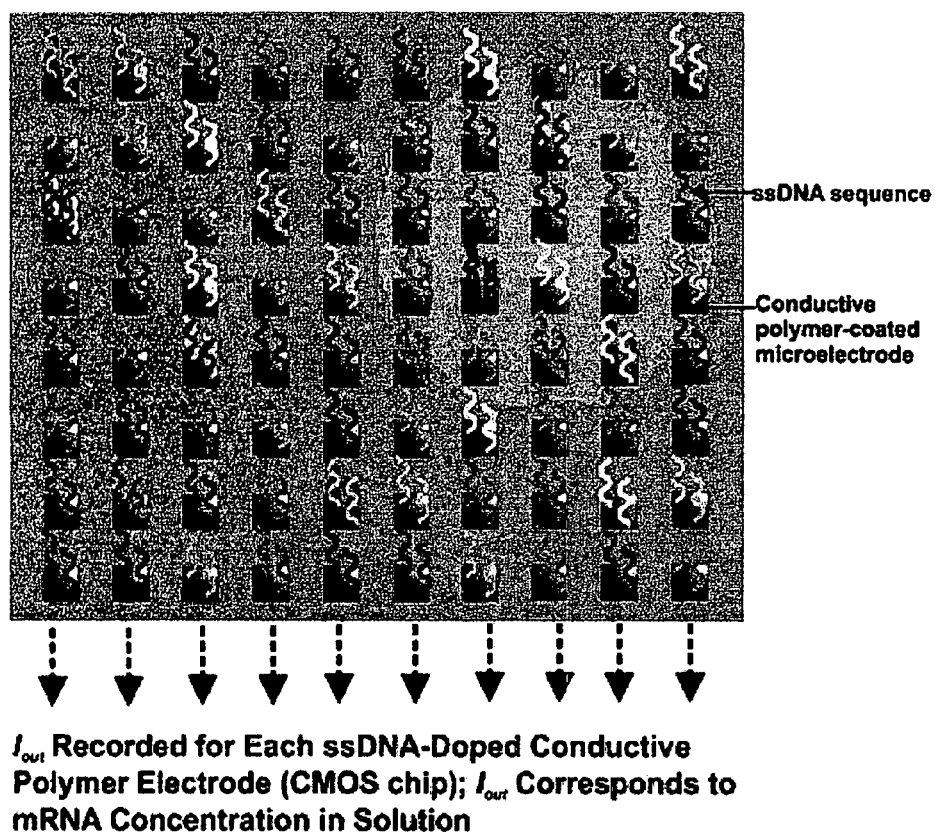
FIG. 30 illustrates the use of integrated conductive polymer microelectrodes and CMOS chips for electrochemical microarrays.
Figure 31:
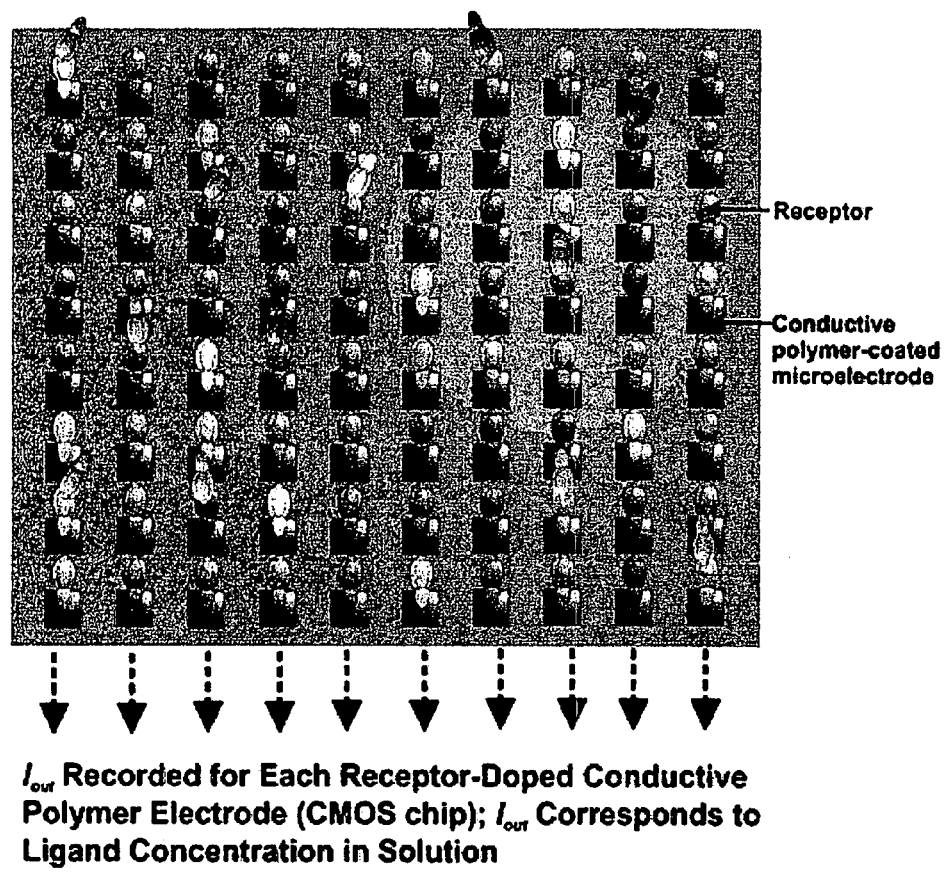
FIG. 31 illustrates the use of integrated conductive polymer microelectrodes and protein/analyte chips.

FIGS. 30 and 31 illustrate the use of integrated conductive polymer microelectrodes and complementary metal-oxide-semiconductor (CMOS) chips for electrochemical microarrays (FIG. 30) or protein/analyte chips (FIG. 31). As shown in FIG. 30, microelectrodes on the top layer of a CMOS chip are functionalized with ssDNA-doped polypyrrole, wherein each microelectrode is doped with a different ssDNA sequence. The complementary mRNA binds to the various ssDNA sequences, and the concentration of mRNA is determined by recording the current at each microelectrode. The current collected at each microelectrode corresponds to the level of ssDNA-mRNA binding at the surface of the polypyrrole matrix. Additionally, a negative potential is applied to reduce the polypyrrole and dissociate the mRNA from the ssDNA, thus permitting dynamic quantification of mRNA concentrations.

Utilizing CMOS technology, amplifiers for each microelectrode are placed on the chip, such that the chip can be placed in a standard IC socket. One can use ssDNA-doped, conductive polymer-coated microelectrodes on CMOS chips to build a reusable microarray that is interfaced with standard data acquisition cards. Similarly, in FIG. 31, the polymer functionalized microelectrodes can be doped with various receptors for ligands of interest, such that the concentration of various proteins and/or analytes in solution can be dynamically quantified based on the recorded current at each microelectrode. These technologies are also used for rapid screening of drug compounds and their effects on various molecular targets. Furthermore, CMOS chips can be packaged to serve as implantable devices; accordingly, the CMOS chips can regulate and quantify ligand concentrations in vitro and in vivo.

Controlled Manipulation of Specific Targets Using Derivatized Conductive Polymer Devices Schematics and results from experiments in which a conductive polymer (polypyrrole) was doped with sulphate ($SO_4^{2-}$) and anti-human fibronectin ($\alpha$FN) antibodies are provided in the FIGS. and Example, below. These experiments were conducted to 1) quantify the current-voltage characteristics of the $\alpha$FN-doped polypyrrole electrodes, 2) characterize the charge transfer kinetics at the polypyrrole-electrolyte interface as a function of applied potential and fibronectin (FN) concentration, and 3) determine if non-specific binding of proteins to polypyrrole is significant. Bovine serum albumin (BSA) was employed as the ligand to examine the ability of proteins to non-specifically bind to functionalized polypyrrole.

The experimental results indicated that the $\alpha$FN-doped polypyrrole films are selective for human fibronectin only and that the extent of fibronectin binding and dissociation was mediated by the voltage applied to the polymer. Control of fibronectin binding to $\alpha$FN antibodies was accomplished by investigating the charge transfer kinetics at the polypyrrole-electrolyte interface, and subsequently exploiting these charge transfer kinetics to modulate fibronectin-$\alpha$FN interactions. The conductive polymer electrodes were found to be useful in measuring fibronectin concentrations in solution.

Figure 2:
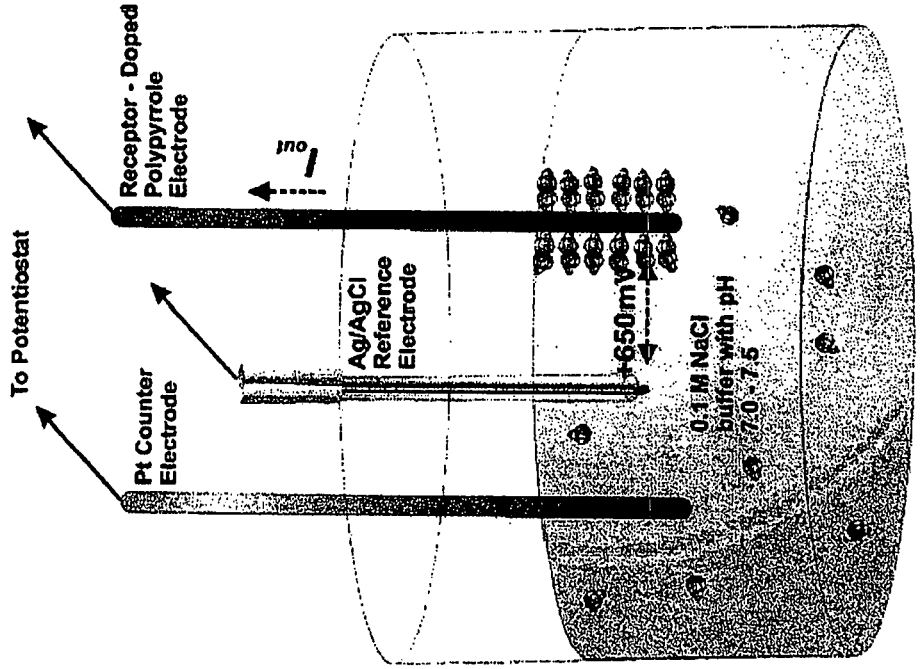

Use of a receptor-doped, polypyrrole-coated electrode to mediate ligand-receptor interactions is illustrated in FIGS. 1 and 2. For the interaction studied in the Example, application of a positive potential facilitates ligand-receptor interactions by oxidizing the polymer (FIG. 1), while application of a negative potential reduces the polymer such that ligands dissociate from receptors entrapped in the polymer matrix, as shown in FIG. 2. By controlling the voltage applied to the polymer, the binding affinity of various ligand-receptor interactions is modulated.

EXAMPLE

In a physiological saline solution, application of a negative potential to PPy films causes $Na^+$ ions to neutralize negative charges present in the polymer. Consequently, interactions between negatively charged antibodies and negatively charged antigens are inhibited during reduction since they impede the ability of the polymer to maintain a charge neutral state.

Conversely, during application of a positive potential to the PPy films (oxidation), the PPy films promote the addition of negative charges to approach a charge neutral state. As a result of the addition of negative charges, negatively charged antibody-antigen interactions occur at the PPy surface during oxidation. Antibodies entrapped in the PPy matrix act as anions, but because of their large size, they cannot move to balance PPy surface charges. Previous studies of sulphate-doped PPy films indicate that $Cl^-$ diffusion into the polymer is not a significant effect in NaCl solutions, and $Cl^-$ will not displace the sulphate polyanions in the PPy. Together, these studies indicate antibody-antigen interactions are reversibly modulated in PPy films by changing the voltage applied to the polymer.

The devices and methods described herein selectively and reversibly mediate protein-protein interactions by exploiting the propensity of antibody-doped PPy to approach a charge neutral state during oxidation and reduction. This method was accomplished by investigating antigen binding to antibody-doped PPy as a function of frequency, applied voltage, and antigen concentration. Impedance measurements indicate that the apparent reversibility of antibody-doped PPy is not due the suppression of strong hydrophobic binding forces, but rather due to the ability of PPy to approach a charge neutral state during polymer oxidation and reduction. The ability to dynamically control antibody-antigen interactions was harnessed to dynamically and selectively modulate FN-$\alpha$FN interactions, as well as to rapidly detect FN concentrations in solution.

The following materials and methods were used to generate the data described herein.

Solution Preparation

Human fibronectin (FN) (BD Biosciences, Franklin Lakes, N.J.) and anti-fibronectin ($\alpha$FN) (Developmental Studies Hybridoma Bank, University of Iowa, Iowa) were used as the antigen and antibody of interest. The $\alpha$FN antibody is directed against the flexible linker between the ninth and tenth type III repeat of human FN. Pyrrole monomer was purchased from Aldrich Chemical Company (St. Louis, Mo.). BSA was purchased from Jackson ImmunoResearch (West Grove, Pa.). The FN, $\alpha$FN, bovine serum albumin and pyrrole were stored at 4° C. until use. Analytical reagent grade $Na_2SO_4$, NaCl, KCl, $CaCl_2$, $MgCl_2$, $NaH_2PO_4$, HEPES [4-(2-hydroxyethyl)-1-piperazineethanesulfonic acid], and glucose were acquired from Aldrich Chemical Company (St. Louis, Mo.). A normal Tyrode's (NT) solution was prepared with (in mmol/L) 135 NaCl, 5.4 KCl, 1.8 CaCl$_2$, 1 MgCl$_2$, 0.33 NaH$_2$PO$_4$, 5 HEPES, and 5 glucose. The pH of the NT solution was equilibrated to 7.40 at 37° C. with the addition of NaOH or HCl in order to remain consistent with previous cell and tissue electrophysiology studies. The pH of the NT solution was 7.49 at 19° C. after equilibration. All solutions were used without purification and were mixed in deionized (18 Ω/cm) water (Millipore, Billerica, Mass.) at 19° C.

Apparatus

A Versatile Modular Potentiostat (Princeton Applied Research, Oak Ridge, Tenn.) was used for electropolymerization, impedance and potentiostatic measurements. The working electrode used for macroscale electrochemical experiments was a 0.25 mm diameter 99.95% gold wire (Alfa Aesar, Ward Hill, Mass.). The reference electrode was an Ag/AgCl saturated KCl electrode (Cypress Systems, Lawrence, Kans.) and a 1.0 mm diameter 99.997% platinum wire (Alfa Aesar, Ward Hill, Mass.) counter electrode. All applied voltages are given versus the Ag/AgCl reference electrode.

Electrode Fabrication

Gold wires were cleaned prior to use by washing with deionized (18 Ω/cm) water followed by sonication for 2 minutes in deionized (18 Ω/cm) water. Pyrrole was electropolymerized galvanostatically on the gold wire to form polypyrrole (PPy) from a solution of 0.1 M pyrrole dissolved in 0.01 M Na$_2$SO$_4$ and was calibrated to pH 7.40 before the addition of antibodies. The pH measurements were carried out using a SympHony pH meter (VWR, West Chester, Pa.) after a two-point 7.00 and 10.00 pH calibration. In order to create αFN-doped PPy films, αFN was included in the electropolymerization solution at a concentration of 200 μg/ml for SPEIS experiments and 360 μg/ml for dose response experiments. Current densities between 1.25 and 2.5 mA/cm$^2$ for a surface area of ~0.08 cm$^2$ were employed for up to 15 minutes versus Ag/AgCl to polymerize the PPy. Oxygen was not removed from the solution during polymerization. After electropolymerization the functionalized electrode was rinsed with deionized water to remove excess pyrrole monomer. Electrodes were conditioned in NT solution containing 1% BSA for more than twenty hours at 4° C. prior to an experiment. The αFN concentrations in solution following electropolymerization were quantified using a SpectraMax M2 spectrophotometer (Molecular Devices, Sunnyvale Calif.) following antibody staining with Bio-Rad Protein Assay concentrate (Bio-Rad, Hercules, Calif.). This step was performed in order to estimate the αFN concentration entrapped in the PPy.

Impedance Analysis

Staircase potential electrochemical impedance spectroscopy (SPEIS) measurements were conducted within the frequency range of 100 kHz to 100 mHz at a voltage amplitude of 20 mV (rms). At each frequency, impedance measurements were collected five times and the average impedance of those five measurements was recorded. Impedance spectra were recorded between −600 mV (vs. Ag/AgCl) and +700 mV (vs. Ag/AgCl) with a voltage step of 87 mV-100 mV. Experiments were conducted in NT solution at 19° C. For various experiments, 250 μg/ml FN or 250 μg/ml BSA were present in the NT solution. In order to determine the impedance response of αFN-doped PPy as a function of FN concentration, experiments were conducted in a NT solution which contained 0, 0.25, 2.5, 25 125, or 250 μg/ml FN. Impedance data were analyzed at +700 mV (vs. Ag/AgCl), since SPEIS experiments indicated that FN binding was highly facilitated at this voltage.

Chronoamperometry

Chronoamperometry (constant voltage) was used to assess the PPy response to various FN concentrations. The αFN-doped PPy electrode was held at +650 mV (vs. Ag/AgCl) for 5 s, and subsequently held at −550 mV (vs. Ag/AgCl) for 95 s. This procedure was repeated 2-3 times, and the PPy was subsequently held at +350 mV (vs. Ag/AgCl) for 15 s to facilitate the relaxation of the electrochemical cell. These applied voltages were selected based on SPEIS results, as well as previous studies of antigen binding in PPy films. Between successive measurements, the system was permitted to equilibrate for an extended period of time and perfused in NT. The current in the PPy was averaged over the last 200 ms of each 5 s oxidizing pulse. Fibronectin concentrations of 0, 0.025, 0.125, 0.25, 1.25, 2.5, 12.5, 25, 125 and 250 μg/ml in NT were examined.

Prediction of FN Concentration

In order to fit the current vs. FN concentration data to a dose response curve, equilibrium binding was assumed using the Hill equation. A quasi-steady state assumption was made since only the last 200 ms of a 5 second pulse were examined, at which time the rate of FN-αFN complex formation should be nearly constant. A four parameter, sigmoidal dose-response function assuming one site competition of a ligand-receptor binding was used to fit the measured αFN-PPy current response:

$$F = F_{min} + \frac{F_{max} - F_{min}}{1 + \left(\frac{X}{EC_{50}}\right)^{HillSlope}} \quad (1)$$

where F is the fraction αFN-doped PPy current response as compared to the PPy current response when all the binding sites are saturated (250 μg/ml of FN present in solution), $F_{min}$ is the fractional response when all the binding sites are saturated (250 μg/ml of FN present in solution), $F_{max}$ is the fractional response when no FN is present in solution, X is the FN concentration, $EC_{50}$ is the FN concentration when the PPy current response is halfway between $F_{min}$ and $F_{max}$, and Hill-Slope is the slope of the dose-response curve. The fractional values of the PPy current response were normalized to the current response when 250 μg/ml of FN was present in solution. This assumption was made since there was no significant change in the PPy current response when 125 μg/ml and 250 μg/ml of FN were present in solution, indicating the αFN binding sites were saturated. The parameter $F_{max}$ represents the fractional PPy current response when no FN was present in solution relative to the PPy current response when 250 μg/ml of FN was present in solution. The constants $EC_{50}$, and HillSlope were approximated using a non-linear least squares fit using Matlab curve fitting toolbox (MathWorks, Natick, Mass.).

Control of Protein Binding with PPy Electrodes

To test the hypothesis that antibody-doped PPy is able to selectively and reversibly modulate antibody-antigen interactions by maintaining a charge neutral state in the PPy film, the ability of αFN-doped PPy films to bind FN in a NT solution was examined. When FN was present in solution, a significant increase in the PPy impedance occurred at frequencies less than 100 Hz as a result of the slow adsorption of FN to αFN antibodies entrapped in the PPy matrix. Impedance measurements indicated that FN adsorption increases the impedance of the polymer in a dose dependent manner. When FN-αFN binding is facilitated at +700 mV (vs. Ag/AgCl), the impedance of the polymer is highly dependent on FN concentration at frequencies less than 2 Hz. When no FN is present in solution, only ion transfer occurs at the polypyrrole-electrolyte interface. The polymer impedance at 0.1-1.0 Hz is two orders of magnitude higher when 250 µg/ml of FN is present in solution. Therefore, the significant increases in polymer impedance can be attributed to protein binding at the polymer surface. This effect is particularly notable at frequencies greater than 2 Hz, when mass transfer effects due to protein adsorption are significant. Although diffusion of ions into the PPy also occurs over these slow timescales, the results demonstrate that the increase in the PPy impedance due to ion diffusion is much smaller than the increase in PPy impedance due to FN adsorption. When no FN is present in solution, only ion transfer occurs at the polypyrrole-electrolyte interface. In this case, the polymer impedance at 0.1-1.0 Hz is one order of magnitude higher when 2.5 µg/ml of FN is present in solution, and two orders of magnitude higher when 250 µg/ml of FN is present in solution. Therefore, the drastic increases in polymer impedance can be attributed to protein binding at the polymer surface.

Furthermore, FN binding increased the charge transfer resistance of the polymer, and minimally altered its double layer capacitance. Thus, increases in impedance during FN binding represented morphological changes in the polymer structure, rather than changes in ionic concentrations at the polymer surface. Grant et al. (Grant, S.; Davis, F.; Law, K. A.; Barton, A. C.; Collyer, S. D.; Higson S. P. J.; Gibson, T. B. *Anal. Chim. Acta.* 2005, 537, 163-168) and Sadik and Xu (Sadik, O. A.; Xu, H. *Anal. Chem.* 2002, 74, 3142-3150) demonstrated that in antibody doped PPy films, the PPy charge transfer resistance increased as a function of the antigen concentration in solution, which is consistent with our results. These data demonstrate that the formation of FN-αFN complexes occurs over slow timescales (>500 ms) and increases the PPy impedance in a dose dependent manner by hindering charge transport in the polymer films.

Reversible Protein Binding by Charge Minimization

Although electrochemical impedance spectroscopy (EIS) is a powerful technique to examine biomolecular and electrochemical interactions, this technique is generally requires that the D.C. voltage is held constant while an impedance spectra is recorded. The unique ability of SPEIS to collect impedance spectra at multiple D.C. voltages provides the framework for comparing D.C. electrochemical data (voltammograms) with kinetic parameters (charge transfer resistances, double layer capacitance, rate constants) that can be measured with EIS. Consequently, SPEIS measurements are sensitive to the magnitude of D.C. voltage, the direction in which the voltage is varied during a potentiodynamic experiment, and the applied A.C. frequency. In particular, SPEIS is a valuable technique to distinguish between adsorption and desorption at an electrode surface, since SPEIS measurements are sensitive to the direction of applied voltage. Because the extent of electrochemical adsorption/desorption often depends on the direction of applied voltage, and electrochemical adsorption kinetics are generally measured using EIS techniques, SPEIS is particularly well-suited for electrochemical adsorption/desorption studies.

Figure 3:
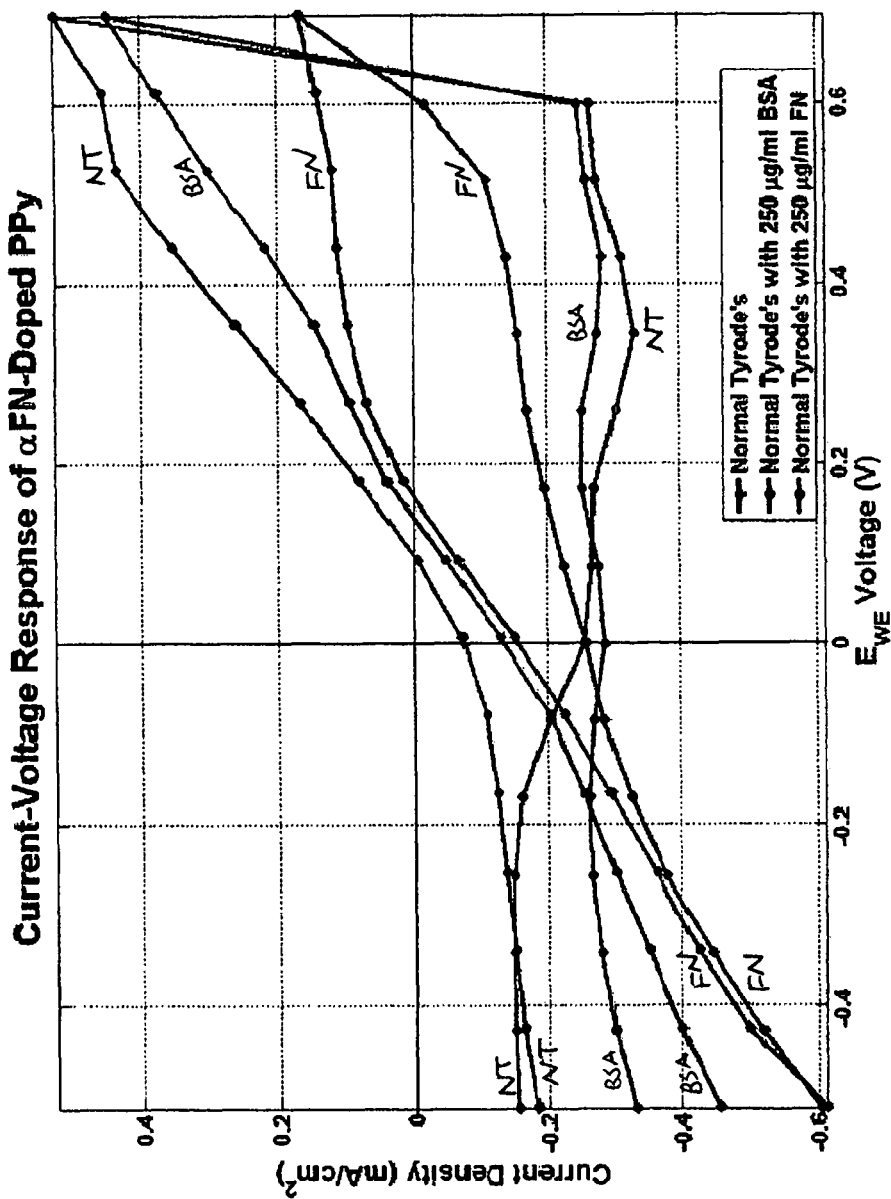
FIG. 3 illustrates forward and reverse step electrochemical impedance spectroscopy results of polypyrrole in a normal Tyrode's (NT) physiological buffer.

In order to demonstrate that αFN-doped PPy films undergo reversible oxidation and reduction in a physiological salt solution, current vs. applied voltage data were collected during SPEIS experiments (FIG. 3). Since BSA has the ability to non-specifically bind to proteins and substrates, it was utilized to verify the molecular specificity of αFN-doped PPy. Application of negative potentials to αFN-doped PPy reduced the polymer films, while application of positive potentials oxidized the polymer films. Although the PPy response displayed a noticeable hysteresis when the polymer was oxidized and subsequently reduced, the polymer response at −514 mV (vs. Ag/AgCl) after oxidation closely resembled the response at −514 mV (vs. Ag/AgCl) preceding oxidation. These data indicate that αFN-doped PPy films undergo reversible oxidation and reduction in a NT solution.

Figure 4:
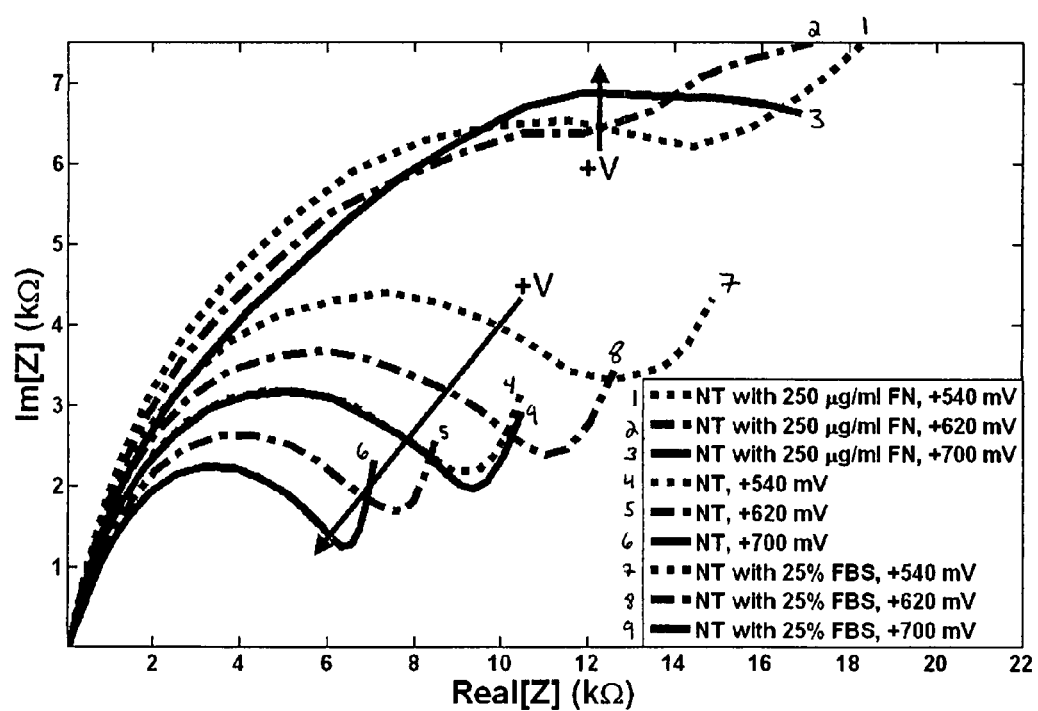
FIG. 4 shows impedance response of αFN-doped PPy in NT, NT with 25% FBS (wt/vol), and NT with 250 µg/ml FN.
Figure 5:
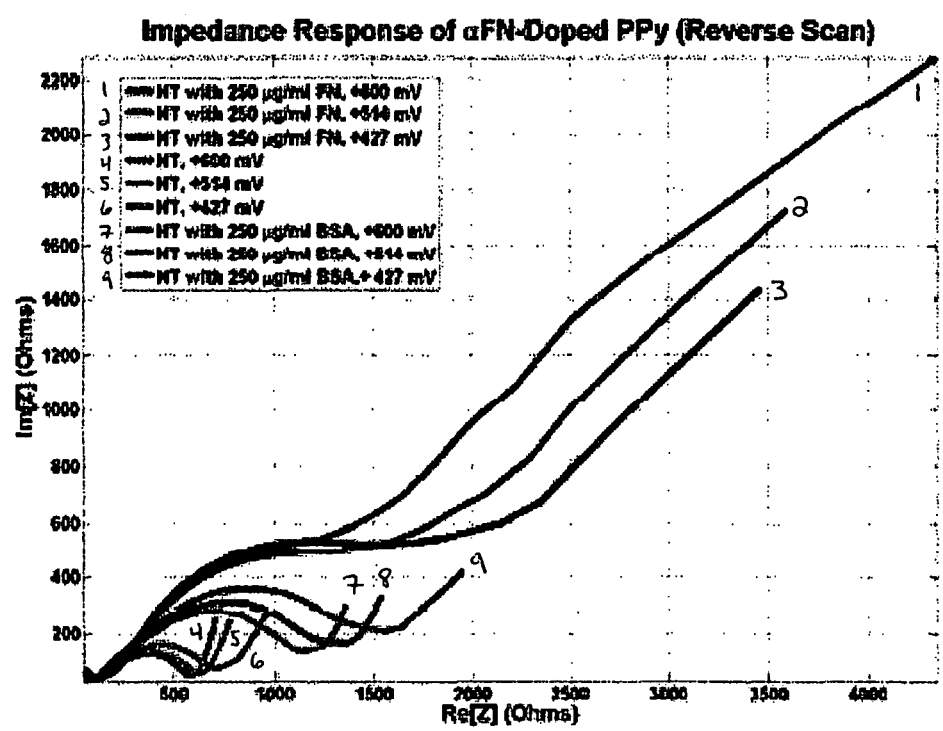
FIG. 5 illustrates impedance response of αFN-doped PPy (reverse scan).
Figure 6:
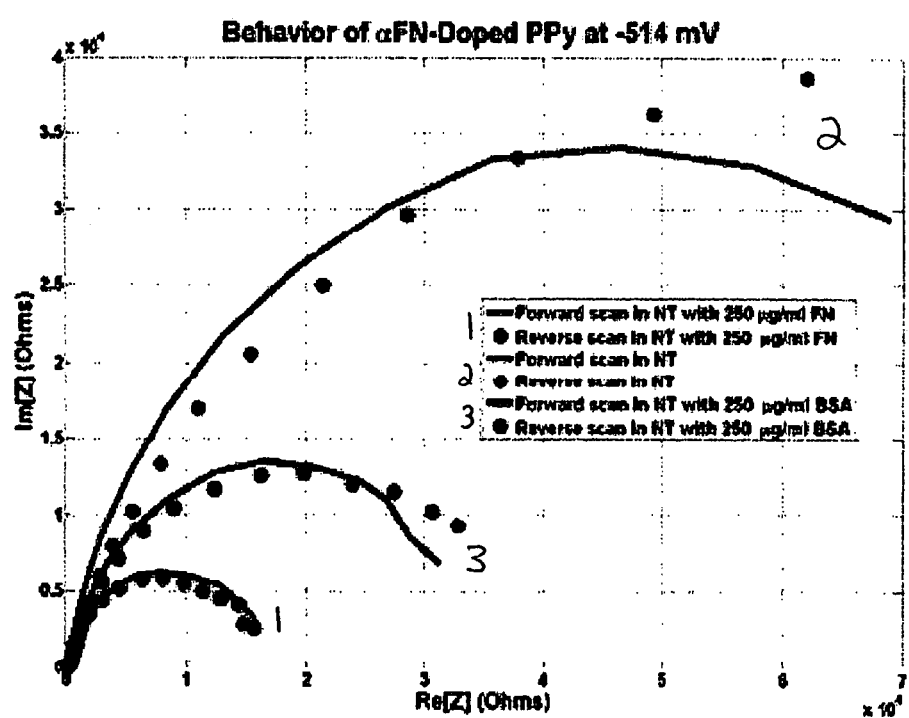
FIG. 6 illustrates the behavior of αFN-doped PPy at −514 mV.
Figure 11:
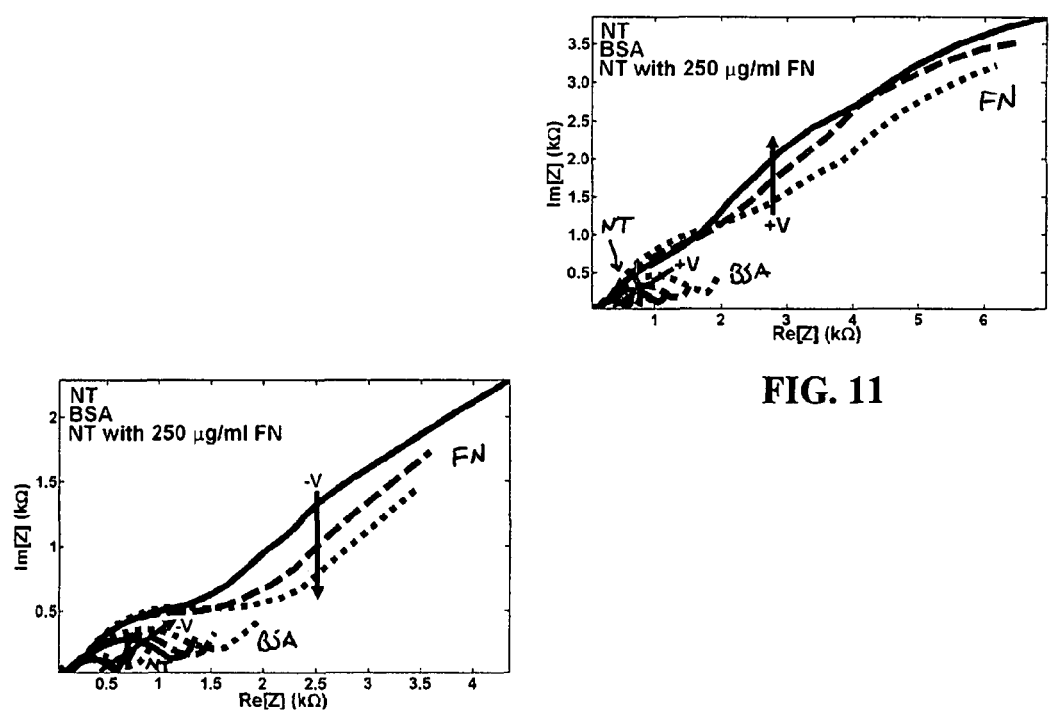
FIGS. 11 and 12 illustrate reversible binding of FN to αFN-doped PPy.

Binding of FN increased the impedance of the αFN-doped polypyrrole by approximately an order of magnitude at low frequencies where adsorption effects are dominant (FIG. 11). However, in solutions containing BSA only, no such increases in impedance were observed. This result demonstrated that the polymer did not facilitate BSA binding or adsorption. Similar experiments were conducted with a 25% fetal bovine serum (FBS) solution in NT which contained bovine FN. Non-specific binding to the polymer was not observed in the 25% FBS/NT solution, further signifying that PPy doped with monoclonal human anti-FN antibodies permits binding of human FN with molecular specificity (FIG. 4). Moreover, human FN and BSA did not bind or adsorb to undoped polypyrrole films, demonstrating that the molecular specificity of the polymer films is critically dependent on the entrapment of αFN antibodies. A comparison of the PPy impedance at −514 mV (vs. Ag/AgCl) before and after polymer oxidation, demonstrates that oxidizing and subsequently reducing the polymer does not significantly affect the overall PPy impedance.

The extent of FN binding is controlled by changing the voltage applied to the αFN-doped PPy. Specifically, when FN was present in solution (FIG. 11), slight changes in applied voltages at which FN-αFN interactions occurred (+400-700 mV, vs. Ag/AgCl) led to appreciable differences in polymer impedance at frequencies where mass transfer effects are significant. These differences in αFN-doped PPy impedance correspond to differences in FN adsorption. The increase in polymer impedance at low frequencies was not as significant in NT and NT with 250 µg/ml BSA, indicating that αFN-doped PPy was exchanging ions with these electrolytes via slow (>200 ms) diffusion and migration processes.

Figure 12:
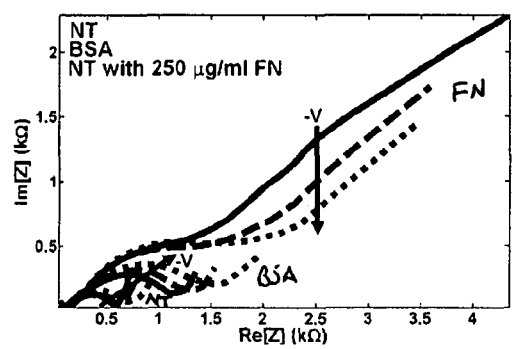

In addition, binding of FN to αFN-doped PPy is selective and reversible. The decreases in αFN-doped PPy impedance in the presence of FN (FIG. 12) can be attributed to FN dissociation from αFN. If FN remained permanently bound to the polymer, the impedance would not decrease significantly upon slight reduction of the polymer. Furthermore, when only ion transfer interactions occurred at the PPy/NT interface (FIG. 11), the total impedance of the PPy increased upon slight reduction. The increase in impedance has been suggested to be due to diffusion of $Na^+$ ions into the polymer matrix to neutralize any negative charges. The decrease in PPy impedance when FN was present in solution is due to the release of negative charges from the PPy instead of the addition of positive ($Na^+$) charges to maintain a charge neutral state. Therefore, the decrease in αFN-immobilized PPy impedance when FN was present in solution (FIG. 11) can be attributed to the dissociation of negatively-charged FN from αFN.

The αFN-doped PPy also did not undergo significant degradation when FN was bound and subsequently released, indicating oxidation and reduction of the polymer is a reversible process. If considerable morphological changes and corrosion occurred within the polymer during these redox reactions and FN adsorption, noticeable differences may be expected in impedance before and after oxidation. However, the similarity in polymer impedance before and after oxidation attests to the reversibility of FN binding to αFN-doped PPy.

Sensor Applications: Dose Response of Antibody-Doped PPy

Figure 7:
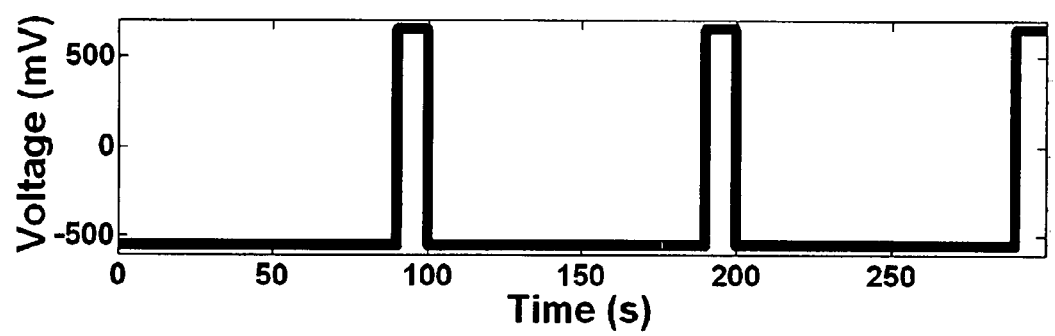
FIGS. 7 and 8 show typical current response of αFN-doped PPy during repeated oxidation and reduction in a NT solution.
Figure 8:
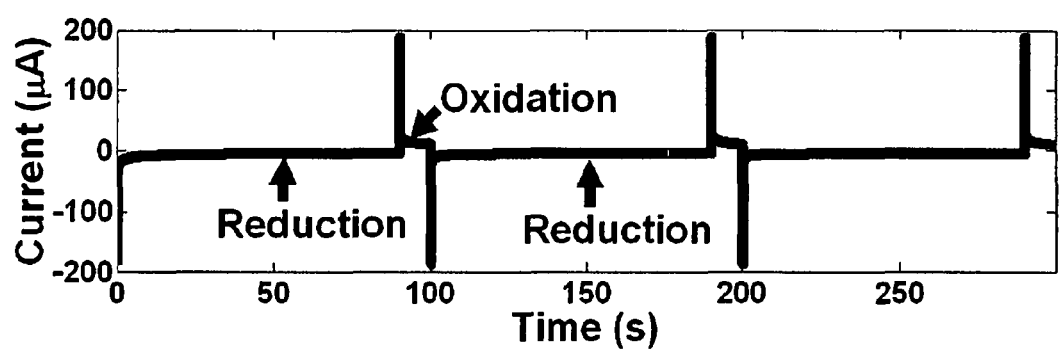

To test the dose response characteristics of αFN-doped PPy, the polymer was switched between oxidized and reduced states in the presence of varying FN concentrations. Oxidation of the αFN-doped PPy was only performed for 5 seconds in order to prevent over-oxidation of the polymer, and the subsequent reduction of the polymer lasted 95 seconds such that the charge on the polymer would reach a quasi-steady state before re-oxidation. An example of a typical current response is shown in FIGS. 7 and 8, where application of the −550 mV (vs. Ag/AgCl) pulses caused a sharp decrease in current, followed by return to a quasi-steady state after 15 seconds. The return to baseline current response in FIGS. 7 and 8 indicates the reversibility of the polymer, where only an average of 2.15±1.22% (n=12 redox cycles) difference was observed in the current response between successive oxidation cycles.

Figure 9:
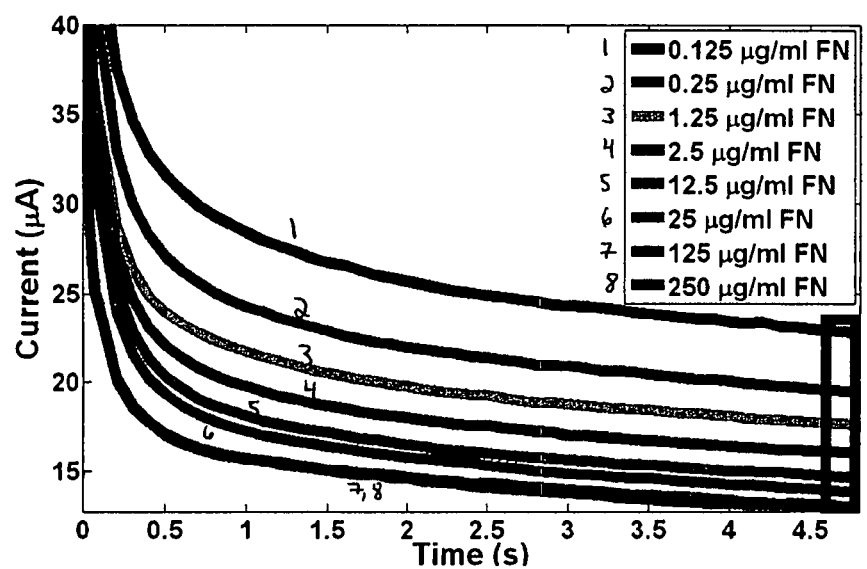
FIGS. 9 and 10 show the response of αFN-doped PPy to various FN concentrations during oxidation.
Figure 10:
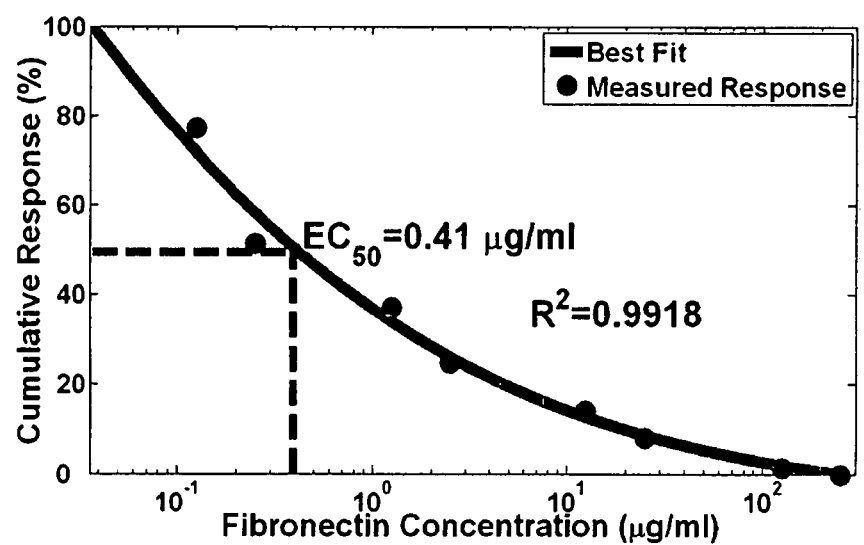

In order to determine the dose response of αFN-doped PPy, the current within the last 200 ms of the 5 second, +650 mV (vs. Ag/AgCl) pulse was averaged (FIG. 9). The current was examined after 5 seconds of oxidation since mass transfer effects due to FN adsorption should be predominant at this timescale, as indicated in FIG. 11. Consequently, only slow interactions were considered when constructing the dose-response curve, during which FN binding had enough time to occur. These data indicate that the charge transfer kinetics at the PPy-electrolyte interface can be manipulated to control antibody-antigen binding in a selective and reversible manner. Moreover, the decrease in current response with increasing FN concentration (FIG. 9) is supported by the impedance results, where greater FN adsorption leads to greater increases in αFN-doped PPy impedance, and thus a decreased current response.

Finally, by measuring the current response as a function of FN concentration, FIG. 11 demonstrates that the antibody-doped PPy can be used as a rapid, re-useable immunosensor. The fractional values of the PPy current response were normalized to the current response when 250 μg/ml of FN was present in solution, since there was no significant change in the PPy current response when 125 μg/ml and 250 μg/ml of FN were present in solution (FIG. 9). Sigmoidal fitting indicated the maximal sensitivity of the αFN-doped PPy to be 0.030 μg/ml, which was consistent with experimental observations of the PPy current response with 0.025 μg/ml of FN present in solution. No change in the PPy current response was observed when 0 and 0.025 μg/ml of FN was present in solution, indicating this low concentration of FN was not detected. The $EC_{50}$ value indicates that the current response decreases to 50% of its maximal value when 0.41 μg/ml (0.9 μM) of FN is present in solution. This result indicates that the αFN-doped PPy can be used for real-time detection of protein concentrations between 300 nM-500 μM.

Implications of Impedance Spectroscopy for Quantifying Protein-Protein Interactions The extent of IgG-αIgG binding was modulated by applying positive (+400 mV vs. Ag/AgCl) pulses for 200 ms to oxidize the PPy and facilitate IgG-αIgG binding. In order to explain the apparent reversibility of IgG binding to αIgG doped PPy, the binding of an antigen with an antibody can be subdivided into primary and secondary reactions. The initial antibody-antigen recognition and binding are dominated by Coloumbic and van der Waals forces. Although these electrostatic forces facilitate antibody-antigen interactions, their total energy constitutes a small fraction of the total binding energy. Secondary bonding forces, such as hydrogen bonding and hydrophobic forces, contribute substantially to the final binding energy, but take much longer to establish. By using 200 ms pulses, this allows the (primary) Coloumbic and van der Waals interactions to occur between IgG and αIgG, but not the secondary binding forces. By allowing only the primary IgG and αIgG interactions to occur, the reversibility of the αIgG-doped PPy is due to the fact that the stronger secondary binding forces between IgG and αIgG are never present.

Figure 13:
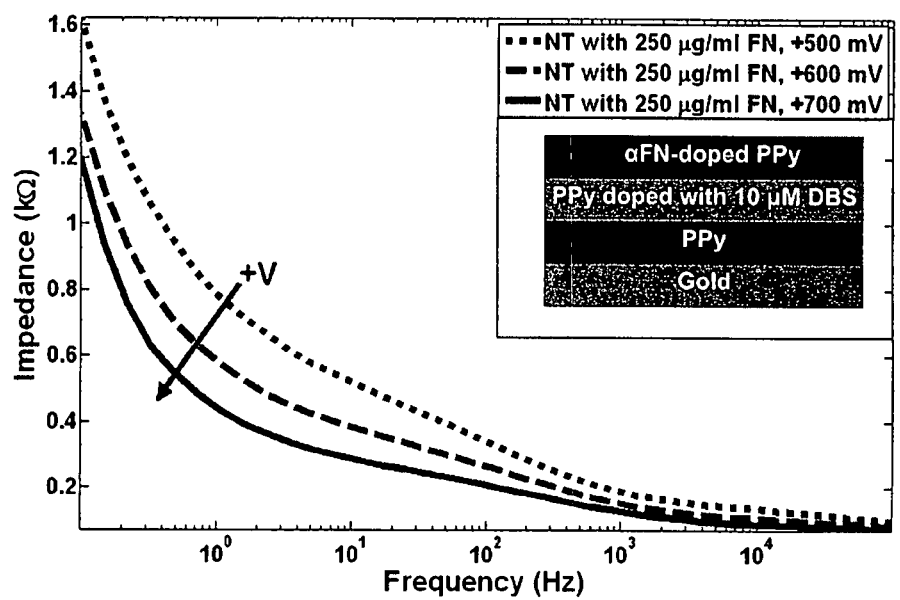
FIG. 13 shows impedance measurements of αFN-doped PPy above a hydrophobic dodecylbenzene sulfonate (DBS)-doped PPy layer (inset).
Figure 14:
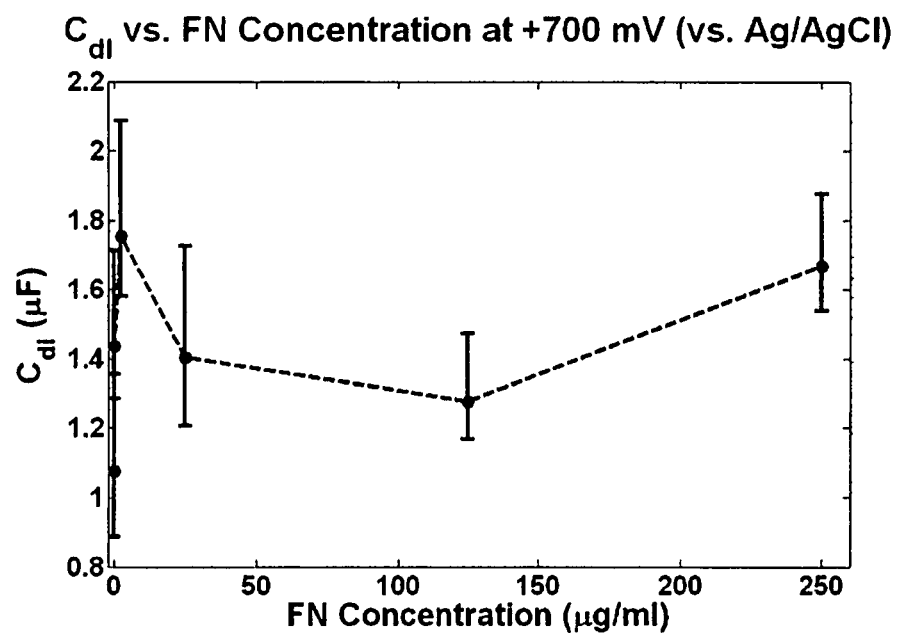
FIG. 14 shows double-layer capacitance of αFN-doped PPy vs. FN concentration.
Figure 15:
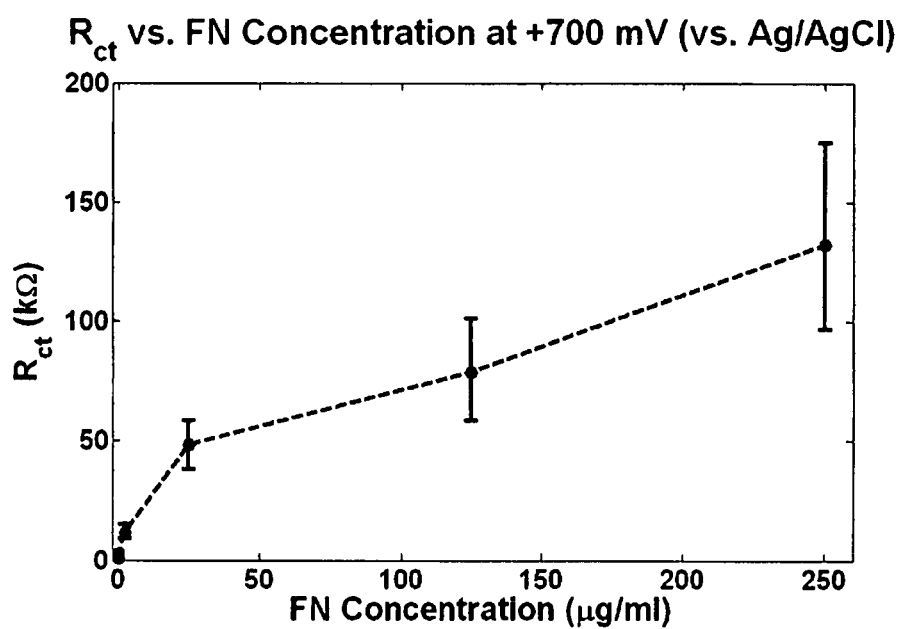
FIG. 15 shows charge transfer resistance of αFN-doped PPy vs. FN concentration.

This data, however, suggest that 200 ms is too short a time period for significant protein adsorption to occur in the PPy matrix. In order to detect notable changes in polymer impedance upon protein adsorption, particularly at high antigen concentrations, the timescale for adsorption to occur is 500 ms or more. At these low frequencies (2 Hz or less) the impedance of the PPy increased significantly, demonstrating that FN is binding to the αFN in the PPy. When FN is not binding to the PPy, no marked increases in impedance are observed at low frequencies (FIG. 11) since ion diffusion does not alter the polymer structure as significantly as antigen binding. In addition, FN can still bind and release from αFN-doped PPy when FN binding is facilitated for 5 seconds, indicating that reversible protein adsorption can occur long after hydrophobic binding forces have been established. Increasing the hydrophobicity of the PPy with dodecylbenzene sulfonate (DBS), a hydrophobic surfactant, did not promote FN-αFN interactions (FIG. 13). Moreover, exchange of ions at the PPy-electrolyte interface occurred on much slower timescales when doped with DBS. This result is be attributed to the fact that the dislocation of π-bonds with a hydrophobic surfactant impeded the ability of the PPy to act as a polymer aggregate, leading to a loose array of pyrrole monomers that did not as readily promote ion exchange and protein-protein interactions. Overall, the results here indicate that the reversibility of antigen binding is not due to the minimization of secondary antibody-antigen binding forces. Rather, the reversibility of antigen binding is due to the minimization of free charges in the PPy during oxidation and reduction. By interacting with $Na^+$ and FN at the PPy-electrolyte interface, the antibody-doped PPy is able to maintain charge neutrality by enhancing or impeding various electrochemical interactions.

The timescale of antigen dissociation depends on affinity constant of the antibody-antigen interaction, where a higher affinity constant leads to a longer dissociation time. If the affinity constant of the antibody-antigen interactions is low, mass transfer processes due to antigen binding and release occurs on a faster timescale, and vise versa for higher antibody-antigen affinity constants. However, the same dose dependent increase in polymer impedance as antigen binding occurs and a subsequent decrease in polymer impedance as the antigen is released such that only the timescale of the antibody-antigen interaction varies with the affinity constant. Consequently, the same trends in polymer impedance are observed for antibody-antigen interactions with different affinity constants, but the timescale of antigen binding and release varies with affinity constant.

Although ion exchange processes barely alter the properties of sulphate-doped PPy films, sulphate dopants have been shown to diffuse out of PPy following neutralization via $Na^+$ cations. Although after the initial oxidation and reduction of the PPy the leakage of sulphate from the PPy should be minimal, some degradation in the PPy response is observed after extended use (15-20 redox cycles), which may be attributed to diffusion of sulphate dopant ions into the electrolyte.

These results demonstrate that antibody-doped PPy are engineered to selectively and reversibly control protein-protein interactions. Impedance spectroscopy results demonstrated that oxidation of the αFN-doped PPy promoted selective FN binding to αFN antibodies and reduction of the polymer films facilitated FN release. Moreover, SPEIS measurements indicated that the apparent reversibility of antibody-doped polypyrrole is due to the minimization of charge in the polymer films during oxidation and reduction. These charge transport characteristics are utilized to selectively and reversibly control FN-αFN interactions, as well as to dynamically detect FN concentrations in solution. Although the specific polymer chemistry utilized depends on the ligand-receptor interaction of interest, functionalized PPy films are successfully used to perform real-time, dynamic measurements of biomolecule concentrations for diagnostic or toxicology screening.

In describing embodiments of the invention, specific terminology is used for the sake of clarity. For purposes of description, each specific term is intended to at least include all technical and functional equivalents that operate in a similar manner to accomplish a similar purpose. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Moreover, while this invention has been shown and described with references to particular embodiments thereof, those skilled in the art will understand that various substitutions and alterations in form and details may be made therein without departing from the scope of the invention; further still, other aspects, functions and advantages are also within the scope of the invention. The contents of all references, including issued patents and published patent applications, cited throughout this application are hereby incorporated by reference in their entirety. The appropriate components and methods of those references may be selected for the invention and embodiments thereof.

What is claimed is:

1. A method for selectively moving a target cell, the method comprising:
    cutting or piercing tissue using a device configured to cut or pierce tissue,
    the device comprising:
        a receptor-doped polymer, the receptor-doped polymer including at least one receptor entrapped in the polymer; and
        a working electrode coated with the receptor-doped polymer, wherein the device is a surgical instrument that binds and removes a target cell;
    contacting a heterogenous population of cells with the device;
    applying an electrical current to manipulate an oxidation or reduction state of the receptor-doped polymer to modulate binding interactions between the at least one receptor and a ligand associated with the target cell;
    binding the ligand associated with the target cell to the at least one receptor; and
    displacing the device from a first location to a second location, wherein the target cell is displaced from the heterogenous population.

2. The method of claim 1, wherein the ligand binds to the at least one receptor upon application of a positive charge to the receptor-doped polymer.

3. The method of claim 1, wherein the ligand is released from binding with the at least one receptor upon application of a negative charge to the receptor-doped polymer.

4. The method of claim 1, wherein the at least one receptor is a cell-specific receptor or cell-binding fragment thereof.

5. The method of claim 1, wherein the at least one receptor is an antibody or fragment thereof.

6. The method of claim 1, wherein the at least one receptor binds to a cell surface antigen of the target cell, wherein the target cell is a eukaryotic or prokaryotic cell.

7. The method of claim 1, wherein the at least one receptor binds to a tumor-specific antigen.

8. The method of claim 1, further comprising:
    releasing the target cell from the receptor-doped polymer after the target cell is displaced.

9. The method of claim 1, wherein applying the electrical current to the receptor-doped polymer enables binding between the at least one receptor and the ligand.

10. The method of claim 1, wherein applying a second electrical current to the receptor-doped polymer enables release of the ligand from binding with the at least one receptor.

11. The method of claim 1, wherein applying the electrical current to the receptor-doped polymer includes applying a first voltage of a first charge to bind the ligand with the at least one receptor and a second voltage of a second opposite charge to release the ligand from binding with the at least one receptor.

12. The method of claim 11, wherein application of one of the first and second voltages manipulates the oxidation or reduction state of the receptor-doped polymer.

13. The method of claim 1, wherein the receptor-doped polymer includes at least one dopant selected from ions, polyions and surfactant molecules embedded in the receptor-doped polymer.

14. The method of claim 13, wherein the at least one dopant is selected from $Cl^-$, $NO_3^-$, $ClO_4^-$, $SO_4^-$, dodecylbenzene sulfonate, $Na^+$, $N^+$, cetyltrimethylammonium chloride, dodecyltrimethylammonium chloride, octyltrimethylammonium chloride, and combinations thereof.

15. The method of claim 1, wherein the at least one receptor is selected from a monoclonal or polyclonal antibody, ssDNA or mRNA sequence, enzyme inhibitor, affinity probe, drug target, protein, biomolecule binding domain, and combinations thereof.

16. The method of claim 15, wherein the at least one receptor is a monoclonal anti-fibronectin antibody.

17. The method of claim 1, wherein the receptor-doped polymer is in the form of a film.

18. The method of claim 1, wherein the receptor-doped polymer has a polyene backbone.

19. The method of claim 18, wherein the polymer is selected from polyacetylene, polyaniline, polypyrrole, polythiopene, and poly(p-phenylene).

20. The method of claim 19, wherein the polymer is polypyrrole.

21. The method of claim 1, wherein the device further comprises a potentiostat electrically coupled with the working electrode.

22. The method of claim 1, wherein the device further comprises a reference electrode and a counter electrode.

23. The method of claim 1, wherein the working electrode is in the form of a scalpel.

24. The method of claim 22, wherein applying the electrical current to the receptor-doped polymer includes applying a voltage to the electrodes to bind the ligand associated with the target cell to the at least one receptor.

25. The method of claim 24, further comprising:
    changing the voltage applied to the electrodes to release the ligand from the at least one receptor after the target cell is displaced.

26. The method of claim 1, wherein the target cell is inside a human body.

27. The method of claim 1, wherein the target cell is a cancer cell or a bacteria cell.

28. The method of claim 1, wherein the device further comprises a semiconductor chip including:
   an array of working electrodes each coated with a conductive polymer film including the at least one receptor; and
   pathways of an electrically conductive material electrically coupled with each working electrode.

29. The method of claim 28, wherein different working electrodes are coated with receptor-doped polymer films including different receptors.

* * * * *